United States Patent
Li et al.

(10) Patent No.: US 10,844,061 B2
(45) Date of Patent: *Nov. 24, 2020

(54) PHARMACEUTICAL COMPOSITIONS COMPRISING 4-(6BR,10AS)-3-METHYL-2,3,6B,9,10,10A-HEXAHYDRO-1H, 7H-PYRIDO[3',4':4,5]PYRROLO[1,2,3-DE]QUINOXALIN-8-YL)-1-(4-FLUORO-PHENYL)BUTAN-1-ONE AND METHODS OF TREATING CONDITIONS OF THE CENTRAL NERVOUS SYSTEM

(71) Applicant: INTRA-CELLULAR THERAPIES, INC., New York, NY (US)

(72) Inventors: Peng Li, New Milford, NJ (US); Qiang Zhang, Plainsboro, NJ (US); Robert Davis, San Diego, CA (US); Lawrence P. Wennogle, Hillsborough, NJ (US)

(73) Assignee: INTRA-CELLULAR THERAPIES, INC., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/591,178

(22) Filed: Oct. 2, 2019

(65) Prior Publication Data

US 2020/0102310 A1   Apr. 2, 2020

Related U.S. Application Data

(63) Continuation of application No. 16/056,143, filed on Aug. 6, 2018, now Pat. No. 10,472,359, which is a continuation of application No. 15/629,481, filed on Jun. 21, 2017, now Pat. No. 10,072,010, which is a continuation of application No. 14/777,466, filed as application No. PCT/US2014/029914 on Mar. 15, 2014, now Pat. No. 9,708,322.

(60) Provisional application No. 61/799,405, filed on Mar. 15, 2013.

(51) Int. Cl.
| | |
|---|---|
| A61K 31/437 | (2006.01) |
| C07D 471/22 | (2006.01) |
| C07D 471/16 | (2006.01) |
| C07D 471/14 | (2006.01) |
| A61K 9/50 | (2006.01) |
| A61K 9/48 | (2006.01) |
| A61K 31/4985 | (2006.01) |
| A61K 47/34 | (2017.01) |
| A61K 47/38 | (2006.01) |

(52) U.S. Cl.
CPC .......... *C07D 471/16* (2013.01); *A61K 9/4825* (2013.01); *A61K 9/4891* (2013.01); *A61K 9/5031* (2013.01); *A61K 31/4985* (2013.01); *A61K 47/34* (2013.01); *A61K 47/38* (2013.01); *C07D 471/14* (2013.01)

(58) Field of Classification Search
CPC ............. A61K 31/437; C07D 471/22

USPC .......................................... 514/288; 544/343
See application file for complete search history.

(56) References Cited

U.S. PATENT DOCUMENTS

| | | |
|---|---|---|
| 2,490,813 A | 12/1949 | Hughes et al. |
| 3,299,078 A | 1/1967 | Pachter |
| 3,813,392 A | 5/1974 | Sellstedt et al. |
| 3,914,421 A | 10/1975 | Rajagopalan |
| 4,001,263 A | 1/1977 | Plattner et al. |
| 4,115,577 A | 9/1978 | Rajagopalan |
| 4,183,936 A | 1/1980 | Rajagopalan |
| 4,219,550 A | 8/1980 | Rajagopalan |
| 4,238,607 A | 12/1980 | Rajagopalan |
| 4,389,330 A | 6/1983 | Tice et al. |
| 4,522,944 A | 6/1985 | Doria et al. |
| 4,530,840 A | 7/1985 | Tice et al. |
| 4,767,628 A | 8/1988 | Hutchinson |
| 4,971,971 A | 11/1990 | Tokunaga et al. |
| 4,985,432 A | 1/1991 | Tokunaga et al. |

(Continued)

FOREIGN PATENT DOCUMENTS

| | | |
|---|---|---|
| GB | 1476087 | 6/1977 |
| WO | WO 2000/064899 | 11/2000 |

(Continued)

OTHER PUBLICATIONS

Hackam et al., "Translation of Research Evidence From Animals to Humans," JAMA, vol. 296(14): 1731-1732 (2006).

(Continued)

*Primary Examiner* — Douglas M Willis
(74) *Attorney, Agent, or Firm* — Hoxie & Associates LLC

(57) ABSTRACT

The invention relates to pharmaceutical compositions comprising compounds of Formula Q:

Formula Q

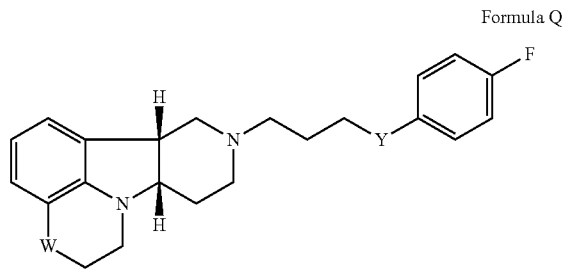

wherein W is N(H)—, or —N(CH$_3$)—, and Y is —C(=O)— or —O—, in free base or pharmaceutically acceptable salt form, and methods of use in the treatment of diseases involving 5-HT$_{2A}$ receptor, serotonin transporter (SERT) pathway and/or the dopamine D$_2$ receptor pathway, and methods of treating conditions of the central nervous system therewith.

17 Claims, No Drawings

(56) References Cited

U.S. PATENT DOCUMENTS

| | | |
|---|---|---|
| 5,114,976 A | 5/1992 | Norden |
| 5,151,419 A | 9/1992 | Perenyi et al. |
| 5,538,739 A | 7/1996 | Bodmer et al. |
| 5,648,539 A | 7/1997 | Goodbrand |
| 5,648,542 A | 7/1997 | Goodbrand et al. |
| 5,654,482 A | 8/1997 | Goodbrand |
| 5,705,697 A | 1/1998 | Goodbrand et al. |
| 5,723,669 A | 3/1998 | Goodbrand et al. |
| 5,723,671 A | 3/1998 | Goodbrand et al. |
| 5,834,493 A | 11/1998 | Quintero et al. |
| 5,902,901 A | 5/1999 | Goodbrand et al. |
| 5,922,338 A | 7/1999 | Brich et al. |
| 6,043,370 A | 3/2000 | Kubo et al. |
| 6,110,921 A | 8/2000 | Mesens et al. |
| 6,323,366 B1 | 11/2001 | Wolfe et al. |
| 6,407,092 B1 | 6/2002 | Hester et al. |
| 6,448,243 B1 | 9/2002 | Kitazawa et al. |
| 6,541,639 B2 | 4/2003 | Zhou et al. |
| 6,548,493 B1 | 4/2003 | Robichaud et al. |
| 6,552,017 B1 | 4/2003 | Robichaud et al. |
| 6,699,852 B2 | 3/2004 | Robichaud et al. |
| 6,713,471 B1 | 3/2004 | Robichaud et al. |
| 6,762,329 B2 | 7/2004 | Marcoux et al. |
| 6,849,619 B2 | 2/2005 | Robichaud et al. |
| 6,849,640 B2 | 2/2005 | Ennis et al. |
| 6,929,803 B2 | 8/2005 | Wong et al. |
| 7,071,186 B2 | 7/2006 | Robichaud et al. |
| 7,081,455 B2 | 7/2006 | Robichaud et al. |
| 7,109,339 B2 | 9/2006 | Lee et al. |
| 7,183,282 B2 | 2/2007 | Robichaud et al. |
| 7,223,870 B2 | 5/2007 | Ghosh et al. |
| RE39,679 E | 6/2007 | Robichaud et al. |
| RE39,680 E | 6/2007 | Robichaud et al. |
| 7,238,690 B2 | 7/2007 | Robichaud et al. |
| 7,244,734 B2 | 7/2007 | Bakker et al. |
| 7,375,226 B2 | 5/2008 | Jolidon et al. |
| 7,462,641 B2 | 12/2008 | Igo et al. |
| 7,592,454 B2 | 9/2009 | Lee et al. |
| 7,614,727 B2 | 11/2009 | Hori |
| 7,645,752 B2 | 1/2010 | McDevitt et al. |
| 7,998,971 B2 | 8/2011 | Barlow et al. |
| 8,309,722 B2 | 11/2012 | Tomesch et al. |
| 8,309,772 B2 | 11/2012 | Weiner et al. |
| 8,461,148 B2 | 6/2013 | Hollander |
| 8,598,119 B2 | 12/2013 | Mates et al. |
| 8,648,077 B2 | 2/2014 | Tomesch et al. |
| 8,779,139 B2 | 7/2014 | Tomesch et al. |
| 8,791,138 B2 | 7/2014 | Seeman et al. |
| 8,993,572 B2 | 3/2015 | Mates et al. |
| 9,168,258 B2 | 10/2015 | Mates et al. |
| 9,199,995 B2 | 12/2015 | Tomesch et al. |
| 9,315,504 B2 | 4/2016 | Tomesch et al. |
| 9,371,324 B2 | 6/2016 | Mates et al. |
| 9,393,192 B2 | 7/2016 | Yam et al. |
| 9,427,412 B2 | 8/2016 | Bryson et al. |
| 9,428,506 B2 | 8/2016 | Mates et al. |
| 9,567,327 B2 | 2/2017 | Xiong et al. |
| 9,586,960 B2 | 3/2017 | Tomesch et al. |
| 9,616,061 B2 | 4/2017 | Mates et al. |
| 9,708,322 B2 | 7/2017 | Li et al. |
| 9,745,300 B2 | 8/2017 | Mates et al. |
| 9,751,883 B2 | 9/2017 | Tomesch et al. |
| 9,956,227 B2 | 5/2018 | Vanover et al. |
| 10,072,010 B2 | 9/2018 | Li et al. |
| 10,077,267 B2 | 9/2018 | Mates et al. |
| 10,117,867 B2 | 11/2018 | Mates et al. |
| 2004/0034015 A1 | 2/2004 | Robichaud et al. |
| 2004/0092534 A1 | 5/2004 | Yam et al. |
| 2004/0127482 A1 | 7/2004 | Robichaud et al. |
| 2004/0142970 A1 | 7/2004 | Chung et al. |
| 2005/0166771 A1 | 8/2005 | Gygi et al. |
| 2005/0182749 A1 | 8/2005 | Matsui |
| 2005/0222209 A1 | 10/2005 | Zeldis et al. |
| 2006/0205787 A1 | 9/2006 | Muller et al. |
| 2008/0069885 A1 | 3/2008 | Mesens et al. |
| 2008/0132552 A1 | 6/2008 | Kleinman et al. |
| 2008/0280941 A1 | 11/2008 | Lourtie |
| 2009/0076159 A1 | 3/2009 | Czarnik |
| 2011/0269777 A1 | 11/2011 | Bachurin et al. |
| 2014/0080816 A1 | 3/2014 | Koolman et al. |
| 2014/0364609 A1 | 12/2014 | Tomesch et al. |
| 2015/0072964 A1 | 3/2015 | Mates et al. |
| 2015/0080404 A1 | 3/2015 | Mates et al. |
| 2015/0166540 A1 | 6/2015 | Mates et al. |
| 2016/0354315 A1 | 12/2016 | Li |
| 2017/0114037 A1 | 4/2017 | Davis et al. |
| 2017/0189398 A1 | 7/2017 | Mates et al. |
| 2017/0319580 A1 | 11/2017 | Yao et al. |
| 2018/0200256 A1 | 7/2018 | Vanover et al. |
| 2019/0071445 A1 | 3/2019 | Li et al. |
| 2019/0231780 A1 | 8/2019 | Yao et al. |

FOREIGN PATENT DOCUMENTS

| | | |
|---|---|---|
| WO | WO 2000/077001 | 12/2000 |
| WO | WO 2000/077002 | 12/2000 |
| WO | WO 2000/077010 | 12/2000 |
| WO | WO 2008/112280 | 9/2008 |
| WO | WO 2009/114181 | 9/2009 |
| WO | WO 2009/145900 | 12/2009 |
| WO | WO 2011/084846 | 7/2011 |
| WO | WO 2011/133224 | 10/2011 |
| WO | WO 2013/155504 | 10/2013 |
| WO | WO 2013/155505 | 10/2013 |
| WO | WO 2013/155506 | 10/2013 |
| WO | WO 2014/145192 | 9/2014 |
| WO | WO 2015/085004 | 6/2015 |
| WO | WO 2015/154025 | 10/2015 |
| WO | WO 2015/154030 | 10/2015 |
| WO | WO 2015/191554 | 12/2015 |
| WO | WO 2017/165755 | 9/2017 |
| WO | WO 2018/106916 | 6/2018 |

OTHER PUBLICATIONS

International Search Report for International Application No. PCT/US2014/29914, dated Aug. 12, 2014, 3 pages.
Jordan, "Tamoxifen: A Most Unlikely Pioneering Medicine," *Nature Reviews*, vol. 2: 205-213 (2003).
Alvir, et al., "Clozapine-Induced Agranulocytosis," *The New England Journal of Medicine*, vol. 329, No. 3, pp. 162-167, (1993).
Balbach, et al., "Pharmaceutical evaluation of early development candidates 'The 100 mg-approach'", *International Journal of Pharmaceutics*, vol. 275, pp. 1-12, (2004).
Bastin, et al.,"Salt Selection and Optimisation Procedures for Pharmaceutical New Chemical Entities", *Organic Process and Research Development*, vol. 4, No. 5, pp. 427-435 (2000).
Bennett, et al., "Cecil Textbook of Medicine," 20th Edition, vol. 1, pp. 1004-1010, (1996).
Bremner, et al., "Neuroimaging of Posttraumatic Stress Disorder", *Psychiatric Annals Journal*, vol. 28, No. 8, p. 445-450, (1998).
Bryan-Lluka, et al., "Potencies of Haloperidol Metabolites as Inhibitors of the Human Noradrenaline, Dopamine and Serotonin Transporters in Transfected COS-7 Cells", *Naunyn-Shemiedeberg's Arch Pharmacol*, vol. 360, pp. 109-115, (1999).
Byrn, et al., "Pharmaceutical Solids: A Strategic Approach to Regulatory Considerations," *Pharmaceutical Research*, vol. 12, No. 7, pp. 945-954, (1995).
Caira, M.R., "Crystalline Polymorphism of Organic Compounds," *Topics in Current Chemistry*, vol. 198, p. 163-203, (1998).
Darmani, et al., "Do Functional Relationships Exist Between $5-HT_{1A}$ and $5-HT_2$ Receptors?" *Pharmacology and Biochemistry & Behavior*, vol. 36, pp. 901-906, (1990).
Davis, et al., "ITI-007 in the Treatment of Schizophrenia: From Novel Pharmacology to Clinical Outcomes," *Expert Review of Neurotherapeutics*, vol. 16, No. 6, pp. 601-614, (2016).
Fawcett, J., "Posttraumatic Stress Disorder, Stress, and Happiness", *Psychiatric Annals Journal*, vol. 28, No. 8, pp. 427-428, (1998).
Foster, et al., "Acetylcholinesterase inhibitors reduce spreading activation in dementia," *Neuropsychologia*, vol. 50, pp. 2093-2099, (2012).

(56) References Cited

OTHER PUBLICATIONS

Friedman, M.J.., "Current and Future Drug Treatment for Post-traumatic Stress Disorder Patients", *Psychiatric Annals Journal*, vol. 28, No. 8, pp. 464-468, (1998).
Grant, D., "Theory and Origin and Polymorphism", *Polymorphism in Pharmaceutical Solids*, Chapter 1, pp. 1-10, (1999).
Guillory, J.K., "Generation of Polymorphs, Hydrates, Solvates, and Amorphous Solids", *Polymorphism in Pharmaceutical Solids*, Chapter 5, pp. 183-226, (1999).
Harbert, et al., "Neuroleptic Activity in 5-Aryltetrahydro-y-carbolines", *J. Med. Chem.*, vol. 23, pp. 635-643, (1980).
Harvey, et al., "Serotonin and Stress: Protective or Malevolent Actions in the Biobehavioral Response to Repeated Trauma?," *Annals of the New York Academy of Sciences*, vol. 1032, pp. 267-272, (2004); DOI: 10.1196/annals.1314.035.
Haynes, et al., "Occurrence of Pharmaceutically Acceptable Anions and Cations in the Cambridge Structural Database", *Journal of Pharmaceutical Sciences*, vol. 94, No. 10, pp. 2111-2120, (2005).
International Preliminary Report on Patentability for International Application No. PCT/US2013/036514 dated Oct. 14, 2014.
International Search Report issued in International Application No. PCT/US2008/003340, dated Aug. 8, 2008, 3 pages.
International Search Report issued in International Application No. PCT/US2009/001608, dated Apr. 27, 2009, 3 pages.
International Search Report issued in International Application No. PCT/US2009/003261, dated Jul. 16, 2009.
International Search Report issued in International Application No. PCT/US2011/00719, dated Jul. 5, 2011, 3 pages.
International Search Report issued in International Application No. PCT/US2013/036515, dated Aug. 13, 2013, 3 pages.
International Search Report issued in International Application No. PCT/US2013/036514, dated Aug. 16, 2013, 3 pages.
International Search Report issued in International Application No. PCT/US2013/036512, dated Aug. 19, 2013, 4 pages.
Izrayelit, L., "Schizoaffective Disorder and PTSD Successfully Treated With Olanzapine and Supportive Psychotherapy", *Psychiatric Annals Journal*, vol. 28, No. 8, pp. 424-426, (1998).
Jain et al., "Polymorphism in Pharmacy", *Indian Drugs*, vol. 23, No. 6, pp. 315-316, (1986).
Kahn, et al., "Residual Symptoms of Schiziphrenia. What are Realistic Treatment Goals? Lingering Symptoms Require you to Evaluate Pharmacotherapy and Offer Psychosocial Interventions," *Current Psychiatry*, vol. 16, No. 3, pp. 35-40, (2017).
Kay, et al., "The Positive and Negative Syndrome Scale (PANSS) for Schizophrenia," *Schizophrenia Bulletin*, vol. 13, No. 2, pp. 261-276, (1987).
Kessler, et al., "Lifetime Prevalence and Age-of-Onset Distributions of DSM-IV Disorders in the National Comorbidity Survey Replication," *Arch Gen Psychiatry*, vol. 62, pp. 593-602, (2005).
Khorana, et al., "Gamma-Carbolines: Binding at 5-HT5A Serotonin Receptors," *Bioorganic & Medicinal Chemistry*, vol. 11, pp. 717-722, p. 718 Table 1, (2003).
Koppel, et al., "Optimal Treatment of Alzheimer's Disease Psychosis: Challenges and Solutions," *Neuropsychiatric Disease and Treatment*, vol. 10, pp. 2253-2262, (2014).
Krystal, J.H., et al., "Adjunctive Risperidone Treatment for Antidepressant-Resistant Symptoms of Chronic Military Service-Related PTSD: A Randomized Trial," *JAMA*, vol. 306, No. 5, pp. 493-502, (2011).
Lebert, et al., "Trazodone in Fronto-Temporal Dementia," *Research and Practice in Alzheimer's Disease*, vol. 11, pp. 356-360, (2006).
Lee, et al. "Novel, Highly Potent, Selective 5-HT$_{2A}$/D$_2$ Receptor Antagonists as Potential Atypical Antipsychotics," *Bioorg. Med. Chem. Lett.*, vol. 13, pp. 767-770, (2003).
Li, et al., "Discovery of a Tetracyclic Quinoxaline Derivative as a Potent and Orally Active Multifunctional Drug Candidate for the Treatment of Neuropsychiatric and Neurological Disorders," *Journal of Medicinal Chemistry*, vol. 57, pp. 2670-2682, (2014).

Lieberman, et al., "ITI-007 for the Treatment of Schizophrenia: A 4-Week Randomized, Double-Blind, Controlled Trial," *Biol. Psychiatry*, vol. 79, No. 12, pp. 952-961, (2015).
Lin, et al., "Dosage and Duration of Antipsychotic Treatment in Demented Outpatients with Agitation or Psychosis," *Journal of the Formosan Medical Association*, vol. 114, pp. 147-153, (2015).
Lipschitz, et al., "Childhood Posttraumatic Stress Disorder: A Review of Neurobiologic Sequelae," *Psychiatric Annals Journal*, vol. 28, No. 8, pp. 452-457, (1998).
Liriano, et al. "Ketamine as treatment for post-traumatic stress disorder: a review." *Drugs in context*, 8:1-7, (2019).
Lopez, et al., "Psychiatric Symptoms Vary with the Severity of Dementia in Probably Alzheimer's Disease," *J. Neuropsychiatry Clin. Neurosc.*, vol. 15, No. 3, pp. 346-353, (2003).
Madhusoodanan, S., et al., "Pharmacological Management of Behavioral Symptoms Associated with Dementia," *World J. Psychiatr.*, vol. 4, No. 4, pp. 72-79, (2014).
Mohamed, et al., "Pharmacotherapy of PTSD in the U.S. Department of Veterans Affairs: Diagnostic- and Symptom-guided Drug Selection," *J. Clin. Psychiatry*, vol. 69, pp. 959-965, (2008).
Morgan, et al., "Acoustic Startle in Individuals With Posttraumatic Stress Disorder," *Psychiatric Annals Journal*, vol. 28, Issue 8, pp. 430-434, (1998).
Newman, et al., "Solid-state Analysis of the Active Pharmaceutical Ingredient in Drug Products," *Drug Discovery Today*, vol. 8, No. 9, pp. 898-903, (2003).
Noble, et al., "The Opiod Receptors as Targets for Drug Abuse Medication," *British Journal of Pharmacology*, vol. 172, pp. 3964-3979, (2015); DOI: 10.1111/bph.13190.
Pieniaszek, et al., "Moricizine Bioavailability via Simultaneous Dual, Stable Isotope Administration: Bioequivalence Implications," *J. Clin. Pharmacol.*, vol. 39, pp. 817-825, (1999).
Pine, et al., "Dopamine, Time, and Impulsivity in Humans," *The Journal of Neuroscience*, vol. 30, No. 26, pp. 8888-8896.
Pond, et al., "Stereospecific Reduction of Haloperidol in Human Tissues," *Biochemical Pharmacology*, vol. 44, No. 5, pp. 867-871, (1992).
Rackova, et al., "Free Radical Scavenging and Antioxidant Activities of Substituted Hexahydropyridoindoles. Quantitative Structure-Activity Relationships." *Journal of Medicinal Chemistry*, vol. 49, No. 8, pp. 2543-2548, (2006).
Rainer, M.K., "Risperidone Long-acting Injection: A Review of its Long Term Safety and Efficacy," *Neuropsychiatric Disease and Treatment*, vol. 4, No. 5, pp. 919-927, (2008).
Rye (Sleep Disorders and Parkinson's Disease, 2000, accessed online http://www.waparkinsons.org/edu_research/articles/Sleep_Disorders.html), 2 pages.
Savjani, et al., "Drug Solubility: Importance and Enhancement Techniques," *International Scholarly Research Network Pharmaceutics*, vol. 2012, pp. 1-10, (2012).
Schennach, et al., "What Are Residual Symptoms in Schizophrenia Spectrum Disorder? Clinical Description and 1-year Persistence Within a Naturalistic Trial," *Eur. Arch. Psychiatry Clin. Neurosci.*, vol. 265, pp. 107-116, (2015); DOI: 10.1007/s00406-014-0528-2.
"Securities," *Bennett v. Alkermes, Inc.*, at http://securities.stanford.edu/filings-documents/1029/ALKS03-01/20031029_r01c_0312091.pdf (retrieved from the internet on Jun. 13, 2017), (2003).
Seishinkei Shi, vol. 110, No. 7, pp. 557-584, (2008); Partial English translation only.
Sigel, et al., "Tenary Complexes in Solution," *Inorganic Chemistry*, vol. 13, No. 2, pp. 462-465, (1974).
Singhal, et al., "Drug Polymorphism and Dosage Form Design: A Practical Perspective," *Advanced Drug Delivery Reviews*, vol. 56, pp. 335-347, (2004).
Skoog, et al., *Principles of Instrumental Analysis*, Fourth Edition, pp. 577, (1992).
Smith, et al., "Oxford Dictionary of Biochemistry and Molecular Biology", *Oxford University Press*, pp. 145, (1997).
Snyder, et al., "Functional Profile of a Novel Modulator of Serotonin, Dopamine, and Glutamate Neurotransmission," *Psychopharmacology*, vol. 232, pp. 605-621, (2015); Published online Aug. 2014, DOI 10.1007/s00213-014-3704-1.

(56) References Cited

OTHER PUBLICATIONS

Southwick, et al., "Neuroendocrine Alterations in Posttraumatic Stress Disorder," *Psychiatric Annals Journal*, vol. 28, No. 8, pp. 436-442, (1998).

Taragano, et al., "A Double-Blind, Randomized, Fixed-Dose Trial of Fluoxetine vs. Amitriptyline in the Treatment of Major Depression Complicating Alzheimer's Disease," *Psychosomatics*, vol. 38, No. 3, pp. 246-252, (1997).

Tariot, et al., "Memantine Treatment in Patients with Moderate to Severe Alzheimer Disease Already Receiving Donepezil: A Randomized Controlled Trail," *JAMA*, vol. 291, No. 3, pp. 317-324, (2004).

Vanover, et al., "Dopamine D2 receptor occupancy of lumateperone (ITI-007): a Positron Emission Tomography Study in patients with schizophrenia," *Neuropsychopharmacology* 44:598-605, (2019).

Vanover, et al., "A Novel Approach to Address an Unmet Need in the Treatment of Schizophrenia and Depression: Lumateperone, an Innovative Modulator of Dopamine, Serotonin, and Glutamate," Abstract presented at the American Society of Clinical Psychopharmacology (ASCP) Annual Meeting; May 29-Jun. 1, 2018; Miami, FL.

Wennogle, et al., "Activation of NMDA and AMPA Receptors by Lumateperone (ITI-007): Implications for Antidepressant Activity," Abstract presented at the 2017 Collegium Internationale Neuro-Psychopharmacologicum (CINP) Thematic Meeting: Treatment Resistant Depression; Jul. 20-22, 2017; Prague.

Weschules, et al., "Acetylcholinesterase Inhibitor and N-Methyl-D-Aspartic Acid Receptor Antagonist Use among Hospice Enrollees with a Primary Diagnosis of Dementia," *Journal of Palliative Medicine*, vol. 11, No. 5, pp. 738-745, (2008).

Wiese, M., "DSC Detection of Polymorphism in Pharmaceutical Anhdrous Dexamethasone Acetate," *TA Instruments*, TA302, pp. 1-4, (2002).

Written Opinion of the International Searching Authority for International Application No. PCT/US2013/036514 dated Aug. 16, 2013, 4 pages.

Yudofsky, et al., "Propranolol in the Treatment of Rage and Violent Behavior in Patients with Chronic Brain Syndromes," *Am. J. Psychiatry*, vol. 138, pp. 218-220, (1981).

Zhang, et al., "The Role of Serotonin 5-HT2A Receptors in Memory and Cognition," *Front. Pharmacol.*, vol. 6, No. 225, pp. 1-17, (2015); DOI: 10.3389/fphar.2015.00225.

Press Release, "Intra-Cellular Therapies Announces Additional Results from Phase I/II Clinical Trail for ITI-007 in Healthy Geriatric Subjects and Patients With Dementia," Intra-Cellular Therapies, Press Release Date: Nov. 21, 2014, (http://ir.intracellulartherapies.com/releasedetail.cfm?ReleaseID=884325), accessed on May 31, 2016.

PHARMACEUTICAL COMPOSITIONS COMPRISING 4-(6BR,10AS)-3-METHYL-2,3,6B,9,10,10A-HEXAHYDRO-1H, 7H-PYRIDO[3',4':4,5]PYRROLO[1,2,3-DE]QUINOXALIN-8-YL)-1-(4-FLUOROPHENYL)BUTAN-1-ONE AND METHODS OF TREATING CONDITIONS OF THE CENTRAL NERVOUS SYSTEM

CROSS REFERENCE TO RELATED APPLICATIONS

This application is a continuation of U.S. application Ser. No. 16/056,143, filed on Aug. 6, 2018, which is a continuation of U.S. application Ser. No. 15/629,481, filed on Jun. 21, 2017, which is a continuation of U.S. application Ser. No. 14/777,466, filed on Sep. 15, 2015, which is a National Stage Entry under 35 U.S.C. § 371 of International Application No. PCT/US2014/029914, filed on Mar. 15, 2014, which claims benefit to and priority from U.S. Provisional Application No. 61/799,405, filed on Mar. 15, 2013, the contents of each of which are hereby incorporated by reference in their entireties.

FIELD OF THE INVENTION

The invention relates to particular substituted heterocycle fused gamma-carbolines, in free, pharmaceutically acceptable salt form, their prodrugs as described herein, pharmaceutical compositions thereof, and methods of use in the treatment of diseases involving 5-HT$_{2A}$ receptor, serotonin transporter (SERT) and/or pathways involving dopamine D$_2$ receptor signaling systems, e.g., diseases or disorders such as anxiety, psychosis, schizophrenia, sleep disorders, sexual disorders, migraine, conditions associated with cephalic pain, social phobias, gastrointestinal disorders such as dysfunction of the gastrointestinal tract motility and obesity; depression and mood disorders associated with psychosis or Parkinson's disease; psychosis such as schizophrenia associated with depression; bipolar disorder; and other psychiatric and neurological conditions, as well as to combinations with other agents.

BACKGROUND OF THE INVENTION

Certain substituted heterocycle fused gamma-carbolines have been reported to be agonists or antagonists of 5-HT2 receptors, particularly 5-HT$_{2A}$ and 5-HT$_{2C}$ receptors, in treating central nervous system disorders. These compounds have been disclosed in U.S. Pat. Nos. 6,548,493; 7,238,690; 6,552,017; 6,713,471; 7,183,282; U.S. RE39680, and U.S. RE39679, as novel compounds useful for the treatment of disorders associated with 5-HT$_{2A}$ receptor modulation such as obesity, anxiety, depression, psychosis, schizophrenia, sleep disorders, sexual disorders migraine, conditions associated with cephalic pain, social phobias, gastrointestinal disorders such as dysfunction of the gastrointestinal tract motility, and obesity. PCT/US08/03340 (WO 2008/112280) and U.S. application Ser. No. 10/786,935 (U.S. Pub. No. 2004/0209864) also disclose methods of making substituted heterocycle fused gamma-carbolines and uses of these gamma-carbolines as serotonin agonists and antagonists useful for the control and prevention of central nervous system disorders such as addictive behavior and sleep disorders. WO 2009/114181 also discloses of methods of preparing toluenesulfonic acid addition salt crystals of these substituted heterocycle fused gamma-carbolines.

In addition, WO/2009/145900 discloses use of particular substituted heterocycle fused gamma-carbolines for the treatment of a combination of psychosis and depressive disorders as well as sleep, depressive and/or mood disorders in patients with psychosis or Parkinson's disease. In addition to disorders associated with psychosis and/or depression, this patent application discloses and claims use of these compounds at a low dose to selectively antagonize 5-HT$_{2A}$ receptors without affecting or minimally affecting dopamine D$_2$ receptors, thereby useful for the treatment of sleep disorders without the side effects of the dopamine D$_2$ pathways or side effects of other pathways (e.g., GABA$_A$ receptors) associated with convention sedative-hypnotic agents (e.g., benzodiazepines) including but not limited to the development of drug dependency, muscle hypotonia, weakness, headache, blurred vision, vertigo, nausea, vomiting, epigastric distress, diarrhea, joint pains, and chest pains.

While these substituted heterocycle fused gamma-carbolines and their uses have been reported, particularly for the treatment of diseases such as schizophrenia, patient compliance in adhering to the medication schedule is a common and critical problem in therapy. According to one study, non-compliance with antipsychotic medication is observed in around 50% of people with schizophrenia. Such non-compliance is linked to the increase in re-hospitalizations and generally poorer outcome in people with psychotic disorders. Therefore, there exists a need for drugs, particularly anti-psychotic drugs that can overcome the non-compliance and provide prodrugs which have a sustained or delayed release profile.

SUMMARY OF THE INVENTION

The present invention provides prodrugs as well as depot formulation of particular substituted heterocycle fused gamma-carbolines that have altered pharmacokinetic profile, e.g., altered rate of absorption and distribution, and therefore may be useful for an improved formulation and/or for controlling the duration of the effect of the drug in the body (e.g., for sustained- or controlled release). The invention therefore provides compounds and their prodrugs, their pharmaceutical composition, for use as set forth herein.

In the first aspect, the invention provides a compound of formula I:

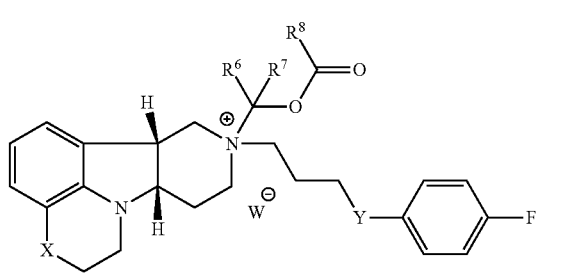

Formula I wherein:
X is —N(H)—, —N(C$_{1-6}$alkyl)- or —O—;
Y is —C(O)—, —O— or —C(H)(OR$^4$)—;
R$^8$ is —C(R$^a$)(R$^b$)(R$^c$), —O—C(R$^a$)(R$^b$)(R$^c$) or —N(R$^d$)(R$^e$);
R$^a$, R$^b$ and R$^c$ are independently H or C$_{1-24}$alkyl;
R$^d$ and R$^e$ are independently H or C$_{1-24}$alkyl;

$R^6$ and $R^7$ are independently H or $C_{1-6}$alkyl;
$R^4$ is H or —C(O)—$C_{1-21}$alkyl; and
$W^-$ is a pharmaceutically acceptable anion.

In a further embodiment of the first aspect, the invention provides the compound of Formula I(a) wherein:
X is —N(H)— or —N(CH$_3$)—;
Y is —C(O)— or —C(H)(OR$^4$)—;
$R^8$ is —C(R$^a$)(R$^b$)(R$^c$), —O—C(R$^a$)(R$^b$)(R$^c$) or —N(R$^d$)(R$^e$);
$R^a$, $R^b$ and $R^c$ are independently H or $C_{1-24}$alkyl;
$R^d$ and $R^e$ are independently H or $C_{1-24}$alkyl;
$R^6$ and $R^7$ are independently H or $C_{1-6}$alkyl;
$R^4$ is H or —C(O)—$C_{1-21}$alkyl; and
W is a pharmaceutically acceptable anion.

In another further embodiment of the first aspect, the invention provides the compound of Formula I(b) wherein:
X is —N(CH$_3$)—;
Y is —C(O)—;
$R^8$ is —C(R$^a$)(R$^b$)(R$^c$), —O—C(R$^a$)(R$^b$)(R$^c$) or —N(R$^d$)(R$^e$);
$R^a$, $R^b$ and $R^c$ are independently H or $C_{1-24}$alkyl;
$R^d$ and $R^e$ are independently H or $C_{1-24}$alkyl;
$R^6$ and $R^7$ are independently H or $C_{1-6}$alkyl;
$W^-$ is a pharmaceutically acceptable anion.

In yet another further embodiment of the first aspect, the invention provides the compound of Formula I, I(a) and I(b) as described in the following formulae:

1.1 the compound of Formula I, wherein X is —N(H)—, —N($C_{1-6}$alkyl)- or —O—;
1.2 the compound of Formula I, wherein X is —O—;
1.3 the compound of Formula I, wherein X is —N($C_{1-6}$alkyl)-, e.g., —N(CH$_3$)—;
1.4 the compound of Formula I, I(a) or I(b), wherein X is —N(CH$_3$)—;
1.5 the compound of Formula I or I(a), wherein X is —N(H)—;
1.6 the compound of Formula I or any of formulae 1.1-1.5, wherein Y is —C(O)—, —O— or —C(H)(OR$^4$)—;
1.7 the compound of Formula I or any of formulae 1.1-1.6, wherein Y is —O—;
1.8 the compound of Formula I, I(a) or I(b) or any of formulae 1.1-1.6, wherein Y is —C(O)—;
1.9 the compound of Formula I or I(a) or any of formulae 1.1-1.6, wherein Y is —C(H)(OR$^4$);
1.10 formula 1.9, wherein $R^4$ is H or —C(O)—$C_{1-21}$alkyl;
1.11 formula 1.9 or 1.10, wherein $R^4$ is H;
1.12 formula 1.9 or 1.10, wherein $R^4$ is —C(O)—$C_{1-21}$alkyl (e.g., —C(O)—$C_{1-5}$alkyl, —C(O)—$C_{6-15}$alkyl or —C(O)-$C_{16-21}$alkyl), preferably said alkyl is a straight chain, saturated or unsaturated and optionally substituted with one or more hydroxy or $C_{1-22}$alkoxy (e.g., ethoxy) groups, for example $R^4$ is —C(O)-$C_6$alkyl, —C(O)-$C_7$alkyl, —C(O)-$C_9$alkyl, —C(O)-$C_{11}$alkyl, —C(O)-$C_{13}$alkyl or —C(O)-$C_{15}$alkyl and such compound hydrolyzes to form the residue of a natural or unnatural, saturated or unsaturated fatty acid, e.g., the compound hydrolyzes to form the hydroxy compound on the one hand and octanoic acid, decanoic acid, dodecanoic acid, tetradecanoic acid or hexadecanoic acid on the other hand);
1.13 formula 1.9 or 1.10, wherein $R^4$ is selected from the group consisting of —C(O)-$C_6$alkyl, —C(O)-$C_7$alkyl, —C(O)-$C_9$alkyl, —C(O)-$C_{11}$alkyl, —C(O)-$C_{13}$alkyl and —C(O)-$C_{15}$alkyl;

1.14 formula 1.9 or 1.10, wherein $R^4$ is —C(O)-$C_{11}$alkyl;
1.15 the compound of Formula I, I(a) or I(b) or any of formulae 1.1-1.14, wherein $R^8$ is —C(R$^a$)(R$^b$)(R$^c$), —O—C(R$^a$)(R$^b$)(R$^c$) or —N(R$^d$)(R$^e$);
1.16 the compound of Formula I, I(a) or I(b) or any of formulae 1.1-1.15, wherein $R^8$ is —C(R$^a$)(R$^b$)(R$^c$);
1.17 the compound of Formula I, I(a) or I(b) or any of formulae 1.1-1.15, wherein $R^8$ is —O—C(R$^a$)(R$^b$)(R$^c$);
1.18 formula 1.16 or 1.17, wherein $R^a$, $R^b$ and $R^c$ are independently H or $C_{1-24}$alkyl;
1.19 any of formulae 1.16-1.18, wherein $R^a$, $R^b$ and $R^c$ are independently $C_{1-24}$alkyl (e.g., selected from the group consisting of $C_2$alkyl, $C_3$alkyl, $C_6$alkyl, $C_8$alkyl, $C_9$alkyl, $C_{11}$alkyl, $C_4$alkyl and $C_{19}$alkyl);
1.20 any of formulae 1.16-1.19, wherein any one of $R^a$, $R^b$ or $R^c$ is H;
1.21 any of formulae 1.16-1.20, wherein one or two of $R^a$, $R^b$ and $R^c$ are independently $C_{1-24}$alkyl (e.g., selected from the group consisting of $C_2$alkyl, $C_3$alkyl, $C_6$alkyl, $C_8$alkyl, $C_9$alkyl, $C_{11}$alkyl, $C_4$alkyl and $C_{19}$alkyl), and the remaining $R^a$, $R^b$ and/or $R^c$ is H;
1.22 the compound of Formula I, I(a) or I(b) or any of formulae 1.1-1.21, wherein $R^8$ is —O—C(H)(CH$_3$)$_2$;
1.23 the compound of Formula I, I(a) or I(b) or any of formulae 1.1-1.21, wherein $R^8$ is —C(CH$_3$)$_3$;
1.24 the compound of Formula I, I(a) or I(b) or any of formulae 1.1-1.15, wherein $R^8$ is —N(R$^d$)(R$^e$) and $R^d$ and $R^e$ are independently H or $C_{1-24}$alkyl;
1.25 formula 1.24, wherein $R^d$ or $R^e$ is $C_{1-24}$alkyl (e.g., selected from the group consisting of $C_2$alkyl, $C_3$alkyl, $C_6$alkyl, $C_8$alkyl, $C_9$alkyl, $C_{11}$alkyl, $C_4$alkyl and $C_{19}$alkyl);
1.26 formula 1.24 or 1.25, wherein $R^d$ and $R^e$ are independently $C_{1-24}$alkyl (e.g., selected from the group consisting of $C_2$alkyl, $C_3$alkyl, $C_6$alkyl, $C_8$alkyl, $C_9$alkyl, $C_{11}$alkyl, $C_4$alkyl and $C_{19}$alkyl);
1.27 formula 1.24 or 1.25, wherein one of $R^d$ or $R^e$ is $C_{1-24}$alkyl (e.g., selected from the group consisting of $C_2$alkyl, $C_3$alkyl, $C_6$alkyl, $C_8$alkyl, $C_9$alkyl, $C_{11}$alkyl, $C_4$alkyl and $C_{19}$alkyl) and the other $R^d$ or $R^e$ is H;
1.28 the compound of Formula I, I(a) or I(b) or any of formulae 1.24-1.27, wherein $R^8$ is —N(H)($C_6$alkyl);
1.29 the compound of Formula I, I(a) or I(b) or any of formulae 1.1-1.28, wherein $R^6$ and $R^7$ are independently H or $C_{1-6}$alkyl;
1.30 the compound of Formula I, I(a) or I(b) or any of formulae 1.1-1.29, wherein $R^6$ and $R^7$ are both H;
1.31 the compound of Formula I, I(a) or I(b) or any of formula 1.1-1.30, wherein $W^-$ is a pharmaceutically acceptable anion;
1.32 the compound of Formula I, I(a) or I(b) or any of formula 1.1-1.31, wherein $W^-$ is a pharmaceutically acceptable anion selected from the group consisting of: Cl$^-$, Br$^-$, I$^-$, HC(O)O$^-$, CH$_3$C(O)O$^-$, CF$_3$C(O)O$^-$, H$_2$PO$_4^-$;
1.33 the compound of Formula I, I(a) or I(b) or any of formulae 1.1-1.32, wherein the compound is selected from:

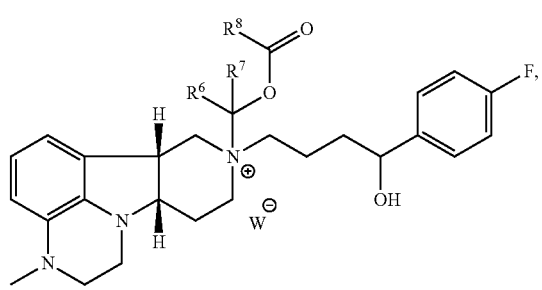

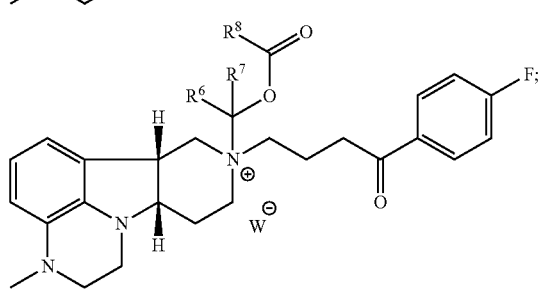

1.34 the compound of Formula I, I(a) or I(b) or any of formulae 1.1-1.33, wherein the compound is selected from:

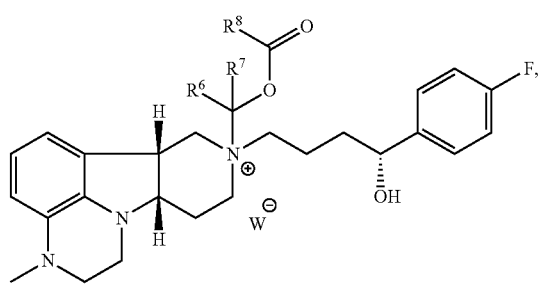

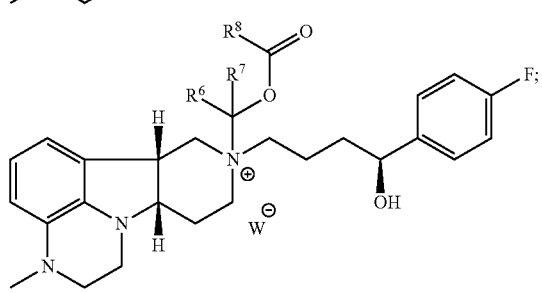

1.35 the compound of Formula I, I(a), I(b) or any of formulae 1.1-1.34, wherein the compound is in substantially pure diastereomeric form (i.e., substantially free from other diastereomers);

1.36 the compound of Formula I, I(a), I(b) or any of formulae 1.1-1.35, wherein the compound has a diasteromeric excess of greater than 70%, preferably greater than 80%, more preferably greater than 90% and most preferably greater than 95%;

1.37 the compound of Formula I, I(a), I(b) or any of the above-referenced formulae wherein the compound is selected from the group consisting of:

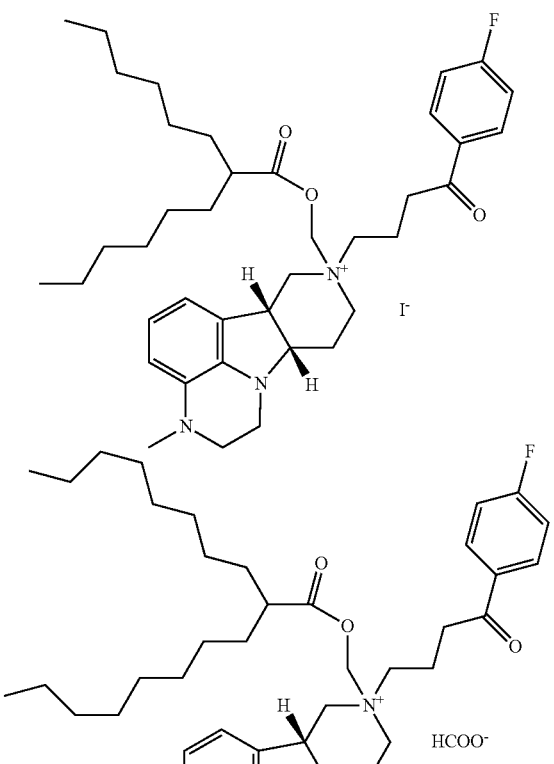

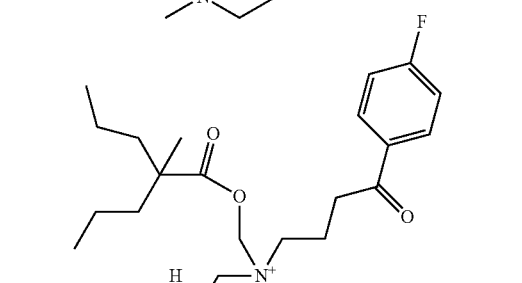

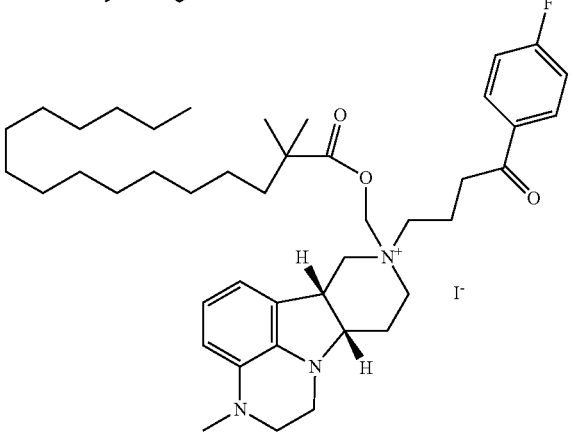

-continued
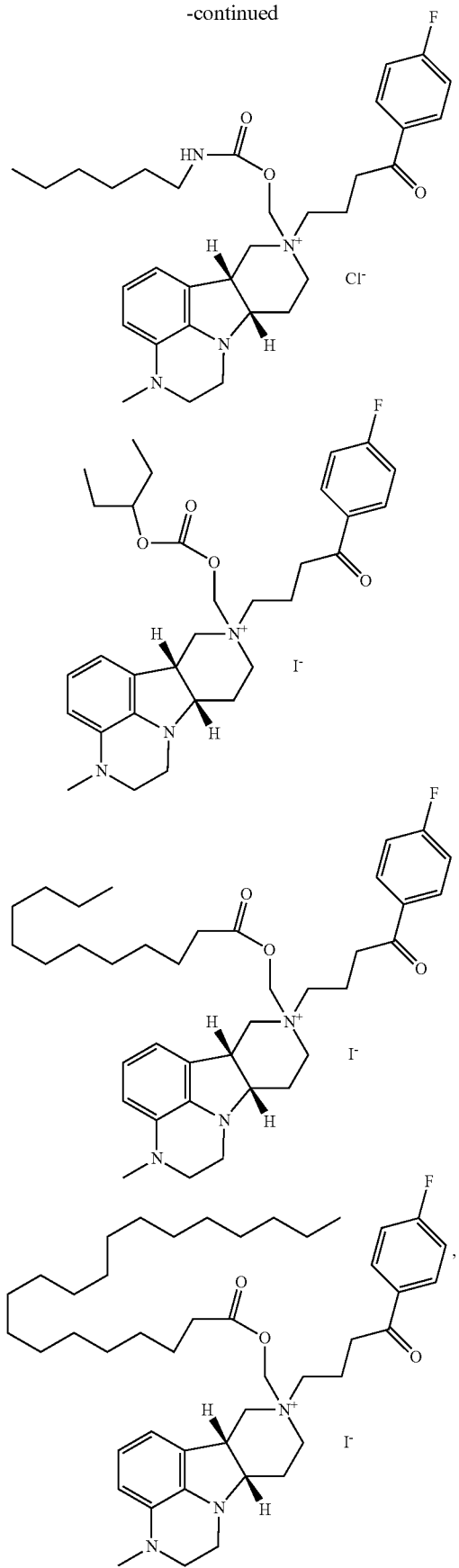
1.38 the compound of Formula I, I(a), I(b) or any of the above-referenced formulae wherein the compound is selected from the group consisting of:
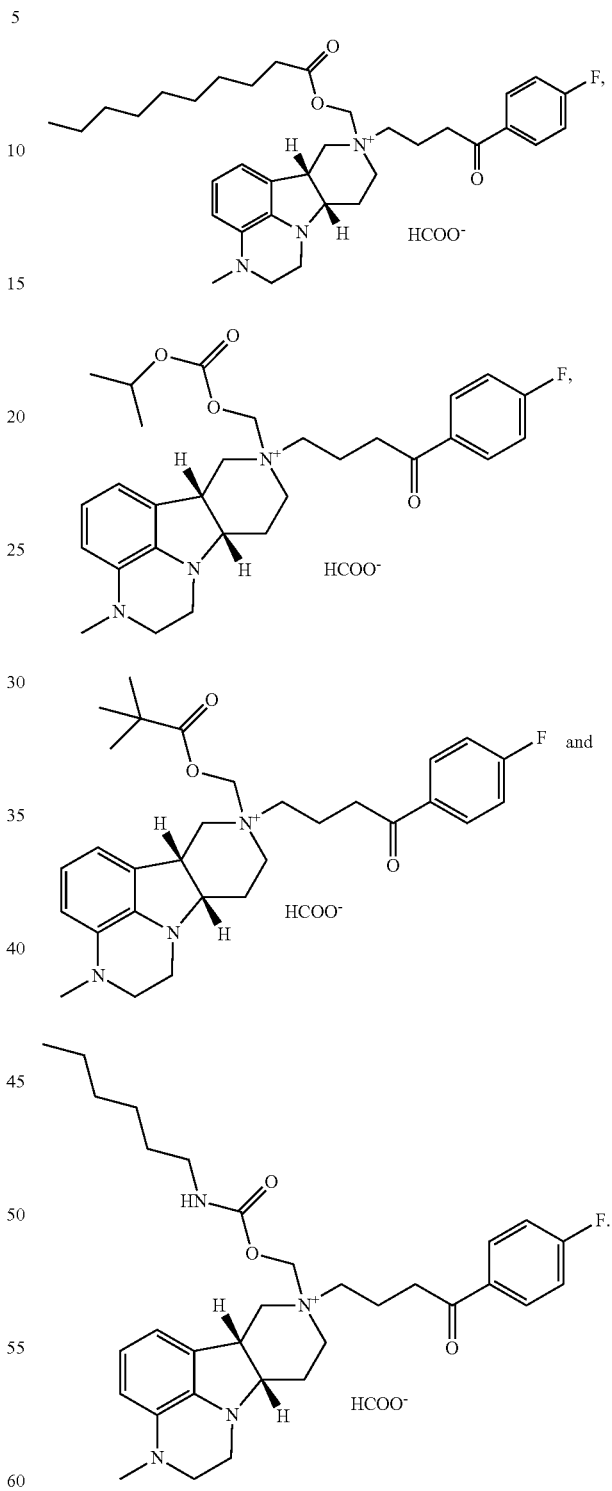
In a particular embodiment, the compound is a compound of formula I(b) wherein $R^8$ is selected from $C_9$alkyl, —O—C(H)(CH$_3$)$_2$, —C(CH$_3$)$_3$ and —N(H)(C$_6$alkyl).
In the second aspect, the invention provides a compound of Formula II:

Formula II

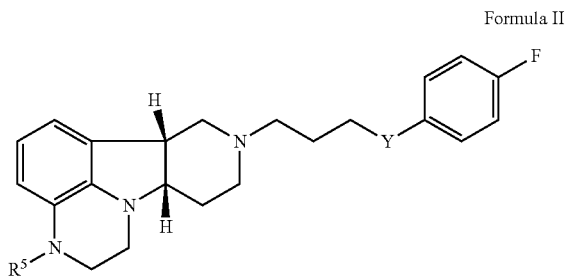

wherein:
Y is —C(O)—, —O— or —C(H)(OR⁴)—;
R⁴ is H or —C(O)—C$_{1-21}$alkyl;
R⁵ is —C(O)—O—C(Rᵃ)(Rᵇ)(Rᶜ) or —C(R⁶)(R⁷)—O—C(O)—R⁸;
R⁸ is —C(Rᵃ)(Rᵇ)(Rᶜ), —O—C(Rᵃ)(Rᵇ)(Rᶜ) or —N(Rᵈ)(Rᵉ);
Rᵃ, R$_b$ and Rᶜ are independently H or C$_{1-24}$alkyl;
Rᵈ and Rᵉ are independently H or C$_{1-24}$alkyl; and
R⁶ and R⁷ are independently H or C$_{1-6}$alkyl;
in free, salt or prodrug form.

In a further embodiment of the second aspect, the invention provides a compound of Formula II(a) wherein:
Y is —C(O)— or —C(H)(OR⁴)—;
R⁴ is H or —C(O)—C$_{1-21}$alkyl;
R⁵ is —C(O)—O—C(Rᵃ)(Rᵇ)(Rᶜ) or —C(R⁶)(R⁷)—O—C(O)—R⁸;
R⁸ is —C(Rᵃ)(Rᵇ)(Rᶜ), —O—C(Rᵃ)(Rᵇ)(Rᶜ) or —N(Rᵈ)(Rᵉ);
Rᵃ, R$_b$ and Rᶜ are independently H or C$_{1-24}$alkyl;
Rᵈ and Rᵉ are independently H or C$_{1-24}$alkyl; and
R⁶ and R⁷ are independently H or C$_{1-6}$alkyl;
in free, salt or prodrug form.

In a further embodiment of the second aspect, the invention provides a compound of Formula II(b) wherein:
Y is —C(O)—;
R⁵ is —C(O)—O—C(Rᵃ)(Rᵇ)(Rᶜ) or —CH₂—O—C(O)—R¹;
R¹ is —C(Rᵃ)(Rᵇ)(Rᶜ), —O—C(Rᵃ)(Rᵇ)(Rᶜ) or —N(Rᵈ)(Rᵉ);
Rᵃ, R$_b$ and Rᶜ are independently H or C$_{1-24}$alkyl;
Rᵈ and Rᵉ are independently H or C$_{1-24}$alkyl; and
R⁶ and R⁷ are independently H or C$_{1-6}$alkyl;
in free, salt or prodrug form.

In yet another further embodiment of the second aspect, the invention provides the compound of Formula II, II(a) and II(b) as described in the following formulae:

2.1. the compound of Formula II, wherein Y is —C(O)—, —O— or —C(H)(OR⁴)—;
2.2. the compound of Formula II or formula 2.1, wherein Y is —O—;
2.3. the compound of Formula II, II(a) or II(b) or formula 2.1, wherein Y is —C(O)—;
2.4. the compound of Formula II, II(a) or formula 2.1, wherein Y is —C(H)(OR⁴);
2.5. the compound of Formula II, II(a) or formula 2.4, wherein R⁴ is H or —C(O)—C$_{1-21}$alkyl;
2.6. the compound of Formula II, II(a) or any of formulae 2.4-2.5, wherein R⁴ is H;
2.7. the compound of Formula II or II(a) or any of formulae 2.4-2.5, wherein R⁴ is —C(O)—C$_{1-21}$alkyl (e.g., —C(O)—C$_{1-5}$alkyl, —C(O)—C$_{6-15}$alkyl or —C(O)—C$_{16-21}$alkyl), preferably said alkyl is a straight chain, saturated or unsaturated and optionally substituted with one or more hydroxy or C$_{1-22}$alkoxy (e.g., ethoxy) groups, for example R⁴ is —C(O)-C$_6$alkyl, —C(O)-C$_7$alkyl, —C(O)-C$_9$alkyl, —C(O)-C$_{11}$alkyl, —C(O)-C$_{13}$alkyl or —C(O)-C$_{15}$alkyl and such compound hydrolyzes to form the residue of a natural or unnatural, saturated or unsaturated fatty acid, e.g., the compound hydrolyzes to form the hydroxy compound on the one hand and octanoic acid, decanoic acid, dodecanoic acid, tetradecanoic acid or hexadecanoic acid on the other hand);
2.8. the compound of Formula II or II(a) or any of formulae 2.4-2.5 and 2.7, wherein R⁴ is selected from the group consisting of —C(O)-C$_6$alkyl, —C(O)-C$_7$alkyl, —C(O)-C$_9$alkyl, —C(O)-C$_{11}$alkyl, —C(O)-C$_{11}$alkyl and —C(O)-C$_{15}$alkyl;
2.9. the compound of Formula II or II(a) or any of formulae 2.4-2.5 and 2.7-2.8, wherein R⁴ is —C(O)-C$_{11}$alkyl;
2.10. the compound of Formula II, II(a) or II(b) or any of formulae 2.1-2.9, wherein R⁵ is —C(O)—O—C(Rᵃ)(Rᵇ)(Rᶜ) or —C(R⁶)(R⁷)—O—C(O)—R⁸;
2.11. the compound of Formula II, II(a) or II(b) or any of formulae 2.1-2.10, wherein R⁵ is —C(R⁶)(R⁷)—O—C(O)—R⁸ and R⁸ is —O—C(Rᵃ)(Rᵇ)(Rᶜ);
2.12. the compound of Formula II, II(a) or II(b) or any of formulae 2.1-2.10, wherein R⁵ is —C(R⁶)(R⁷)—O—C(O)—R⁸ and R⁸ is —C(Rᵃ)(Rᵇ)(Rᶜ);
2.13. any of formulae 2.10-2.12, wherein Rᵃ, Rᵇ and Rᶜ are independently H or C$_{1-24}$alkyl (e.g., selected from the group consisting of C$_2$alkyl, C$_3$alkyl, C$_6$alkyl, C$_8$alkyl, C$_9$alkyl, C$_{11}$alkyl, C$_4$alkyl and C$_{19}$alkyl);
2.14. any of formulae 2.10-2.13, wherein Rᵃ, Rᵇ and Rᶜ are independently C$_{1-24}$alkyl (e.g., selected from the group consisting of C$_2$alkyl, C$_3$alkyl, C$_6$alkyl, C$_8$alkyl, C$_9$alkyl, C$_{11}$alkyl, C$_4$alkyl and C$_{19}$alkyl);
2.15. any of formulae 2.10-2.14, wherein Rᵃ, Rᵇ and Rᶜ are independently H;
2.16. any of formulae 2.10-2.15, wherein one or two of Rᵃ, Rᵇ and Rᶜ are independently C$_{1-24}$alkyl (e.g., selected from the group consisting of C$_2$alkyl, C$_3$alkyl, C$_6$alkyl, C$_8$alkyl, C$_9$alkyl, C$_{11}$alkyl, C$_4$alkyl and C$_{19}$alkyl), and the remaining Rᵃ, Rᵇ and/or Rᶜ is H;
2.17. the compound of Formula II, II(a) or II(b) or any of formulae 2.10-2.16, wherein R⁸ is —O—C(H)(CH$_3$)$_2$;
2.18. the compound of Formula II, II(a) or II(b) or any of formulae 2.10-2.16, wherein R⁸ is —C(CH$_3$)$_3$;
2.19. the compound of Formula II, II(a) or II(b) or any of formulae 2.1-2.10, wherein R⁵ is —C(R⁶)(R⁷)—O—C(O)—R⁸ and R⁸ is —N(Rᵈ)(Rᵉ);
2.20. formula 2.19, wherein Rᵈ and Rᵉ are independently H or C$_{1-24}$alkyl;
2.21. formula 2.19 or 2.20, wherein both Rᵈ and Rᵉ are independently C$_{1-24}$alkyl (e.g., selected from the group consisting of C$_2$alkyl, C$_3$alkyl, C$_6$alkyl, C$_8$alkyl, C$_9$alkyl, C$_{11}$alkyl, C$_4$alkyl and C$_{19}$alkyl);

2.22. formula 2.19 or 2.20, wherein $R^d$ or $R^e$ is H;
2.23. formula 2.19 or 2.22, wherein one of $R^d$ or $R^e$ is $C_{1-24}$alkyl (e.g., selected from the group consisting of $C_2$alkyl, $C_3$alkyl, $C_6$alkyl, $C_8$alkyl, $C_9$alkyl, $C_{11}$alkyl, $C_4$alkyl and $C_{19}$alkyl) and the other $R^d$ or $R^e$ is H;
2.24. the compound of Formula II, II(a) or II(b) or any of formulae 2.19-2.23, wherein $R^8$ is —N(H)($C_6$alkyl);
2.25. the compound of Formula II, II(a) or II(b) or any of formulae 2.1-2.24-, wherein $R^6$ and $R^7$ are independently H or $C_{1-6}$alkyl;
2.26. the compound of Formula II, II(a) or II(b) or any of formulae 2.1-2.24, wherein $R^6$ and $R^7$ are both H;
2.27. the compound of Formula II, II(a) or II(b) or any of form formulae 2.1-2.27, wherein $W^-$ is a pharmaceutically acceptable anion;
2.28. the compound of Formula II, II(a) or II(b) or any of formula 2.1-2.27, wherein $W^-$ is a pharmaceutically acceptable anion selected from the group consisting of: $Cl^-$, $Br^-$, $I^-$, $HC(O)O^-$, $CH_3C(O)O^-$, $CF3C(O)O^-$, $H_2PO_4^-$;
2.29. the compound of Formula II, II(a) or II(b) or any of formulae 2.1-2.28, wherein the compound is selected from:

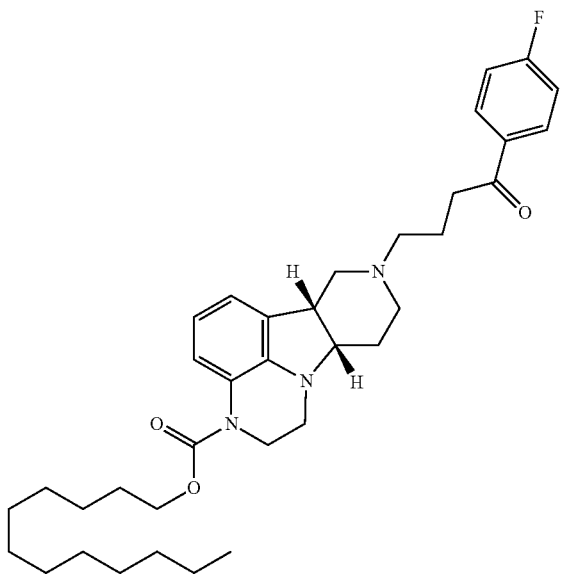

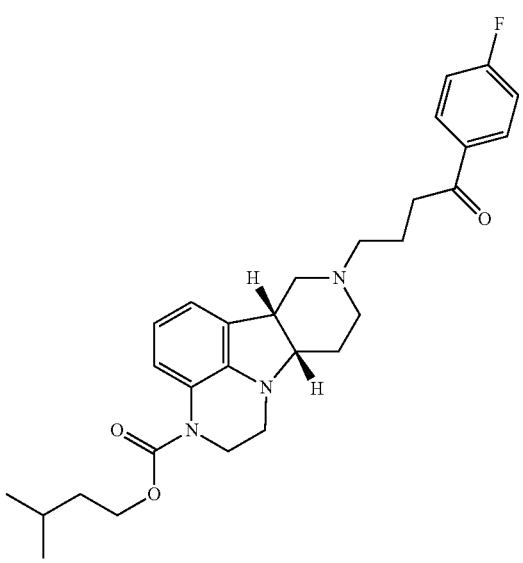

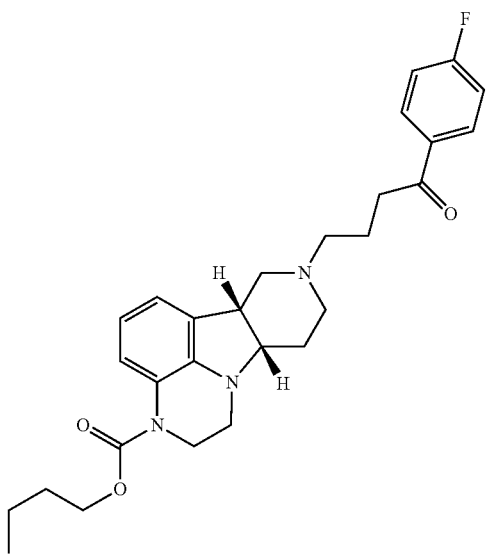

-continued
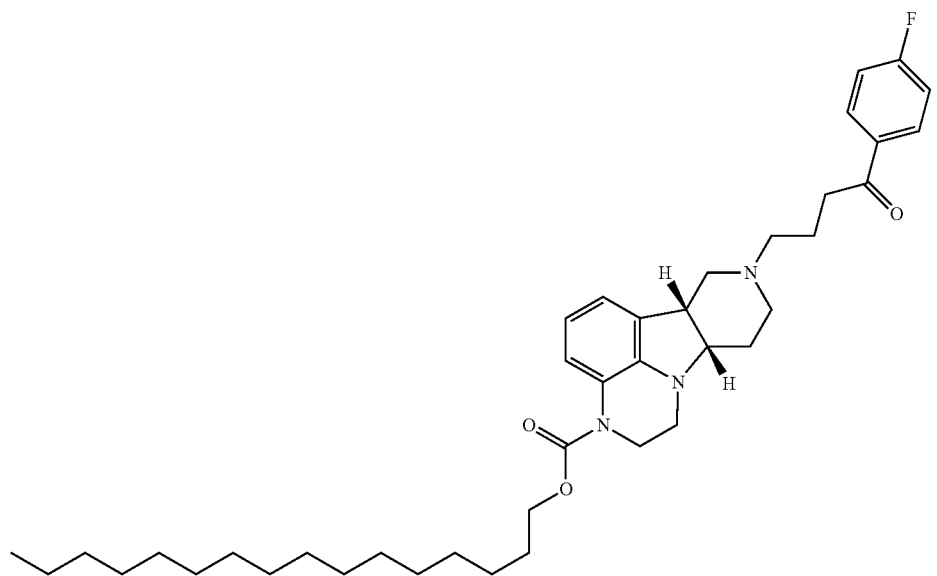
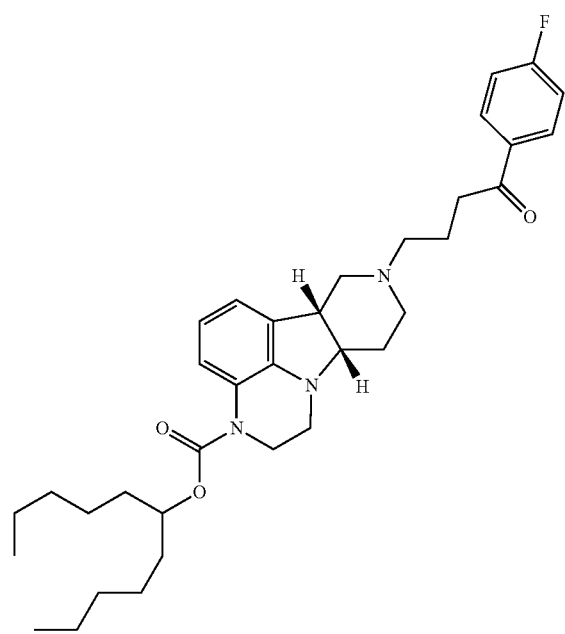

-continued
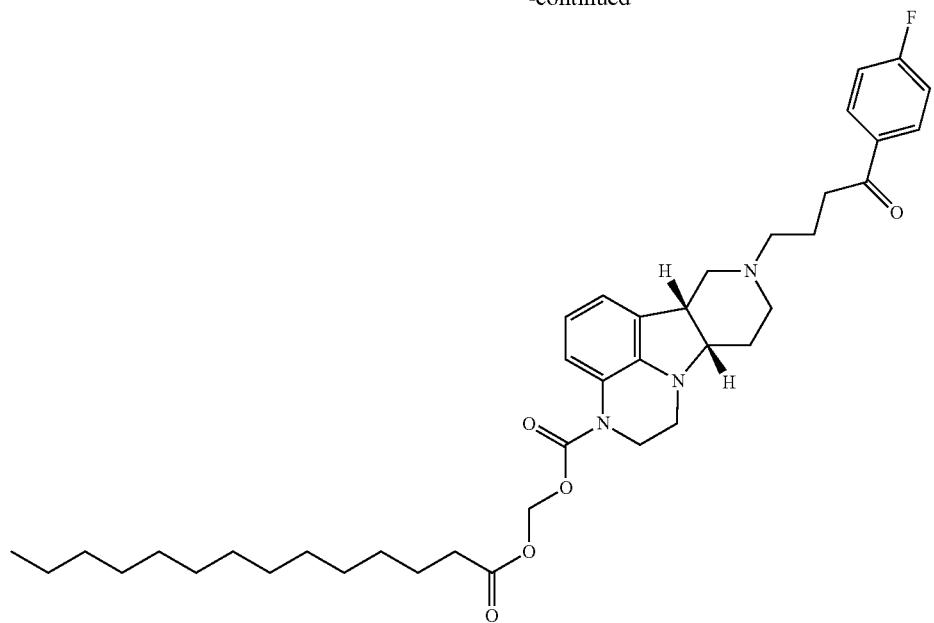
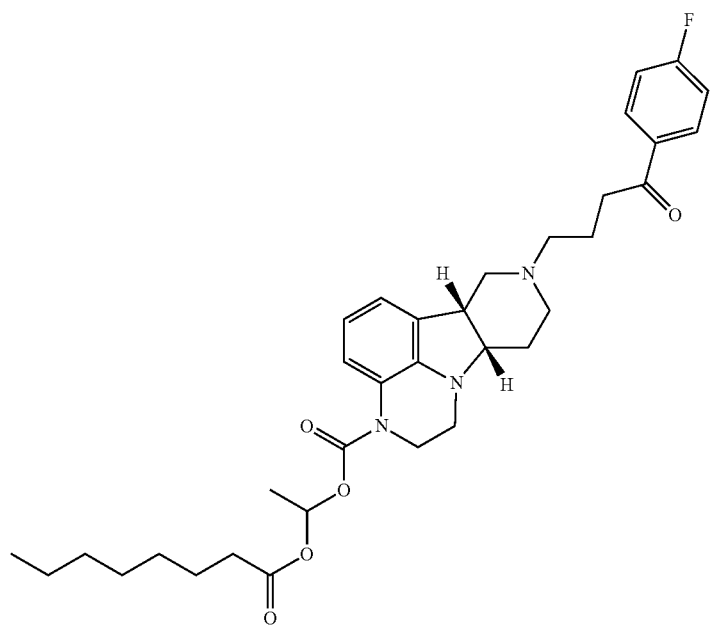

-continued

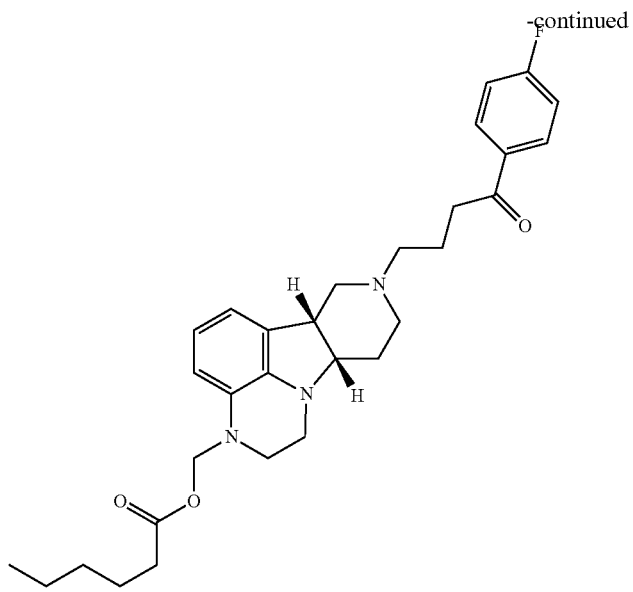

2.30. the compound of Formula II, II(a) or II(b) or any of formulae 2.1-2.29, wherein the compound is in substantially pure diastereomeric form (i.e., substantially free from other diastereomers);

2.31. the compound of Formula II, II(a) or II(b) or any of formulae 2.1-2.30, wherein the compound has a diasteromeric excess of greater than 70%, preferably greater than 80%, more preferably greater than 90% and most preferably greater than 95%;

in free, salt or prodrug form.

In the third aspect, the invention provides a compound of Formula III:

Formula III

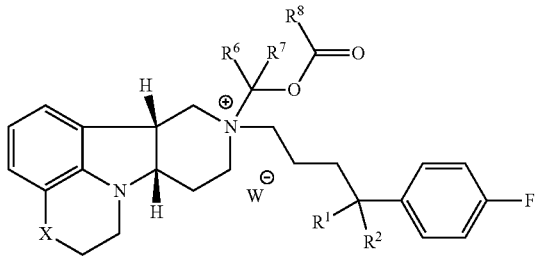

wherein:

X is —N(H)—, —N($C_{1-4}$alkyl)- or —O—;

$R^8$ is —C($R^a$)($R^b$)($R^c$), —O—C($R^a$)($R^b$)($R^c$) or —N($R^d$)($R^e$);

$R^a$, $R^b$ and $R^c$ are independently H or $C_{1-24}$alkyl;

$R^d$ and $R^e$ are independently H or $C_{1-24}$alkyl;

$R^6$ and $R^7$ are independently H or $C_{1-6}$alkyl;

$R^1$ is H or $C_{1-6}$alkyl (e.g., methyl);

$R^2$ is H or $OR^3$ wherein $R^3$ is H, $C_{1-6}$alkyl (e.g., methyl) or —C(O)—$C_{1-21}$alkyl, provided that $R^1$ and $R^2$ are not both H, $R^1$ and $R^3$ are not both H, and when $R^3$ is —C(O)—$C_{1-21}$alkyl, $R^1$ is $C_{1-6}$alkyl (e.g., methyl); and $W^-$ is a pharmaceutically acceptable anion.

In a particular embodiment of the third aspect, the compound of Formula III is a compound wherein:

X is —N(H)—, —N($C_{1-4}$alkyl)- or —O—;

$R^8$ is —C($R^a$)($R^b$)($R^c$), —O—C($R^a$)($R^b$)($R^c$) or —N($R^d$)($R^e$);

$R^a$, $R^b$ and $R^c$ are independently H or $C_{1-24}$alkyl;

$R^d$ and $R^e$ are independently H or $C_{1-24}$alkyl;

$R^6$ and $R^7$ are independently H or $C_{1-6}$alkyl;

$R^1$ is H or $C_{1-6}$alkyl (e.g., methyl);

$R^2$ is H or $OR^3$ wherein $R^3$ is H or $C_{1-6}$alkyl (e.g., methyl), provided that $R^1$ and $R^2$ are not both H, and $R^1$ and $R^3$ are not both H; and $W^-$ is a pharmaceutically acceptable anion.

In a further embodiment of the third aspect, the invention provides a compound of Formula III as hereinbefore described as follows:

3.1 the compound of Formula III, wherein $R^2$ is $OR^3$, wherein $R^3$ is H, $C_{1-6}$alkyl (e.g., methyl) or —C(O)—$C_{1-21}$alkyl, provided that $R^1$ and $R^2$ are not both H, $R^1$ and $R^3$ are not both H, and when $R^3$ is —C(O)—$C_{1-21}$alkyl, $R^1$ is $C_{1-6}$alkyl (e.g., methyl);

3.2 the compound of Formula III or 3.1, wherein $R^1$ is $C_{1-6}$alkyl (e.g., methyl);

3.3 the compound of Formula III, 3.1 or 3.2, wherein $R^1$ is methyl;

3.4 the compound of Formula III or any of formulae 3.1-3.3, wherein $R^2$ is $OR^3$ and $R^3$ is $C_{1-6}$alkyl (e.g., methyl);

3.5 the compound of Formula III or any of formulae 3.1-3.4, wherein $R^2$ is $OR^3$ and $R^3$ is methyl;

3.6 the compound of Formula III or any of formulae 3.1-3.3, wherein $R^2$ is $OR^3$ and $R^3$ is H, provided that $R^1$ and $R^2$ are not both H and $R^1$ and $R^3$ are not both H;

3.7 the compound of Formula III or any of formulae 3.1-3.3, wherein $R^2$ is $OR^3$ and $R^3$ is —C(O)—$C_{1-21}$alkyl;

3.8 the compound of Formula III or any of formulae 3.1-3.7, wherein X is N(H), N($C_{1-4}$alkyl) or O;

3.9 the compound of Formula III or any of formulae 3.1-3.7, wherein X is —O—;

3.10 the compound of Formula III or any of formulae 3.1-3.7, wherein X is —N(H)—;

3.11 the compound of Formula III or any of formulae 3.1-3.7, wherein X is —N(C$_{1-4}$alkyl)-;

3.12 the compound of Formula III or any of formulae 3.1-3.7, wherein X is —N(CH$_3$)—;

3.13 the Compound of Formula III or any of formulae 3.1-3.12, wherein the Compound is:

Formula III

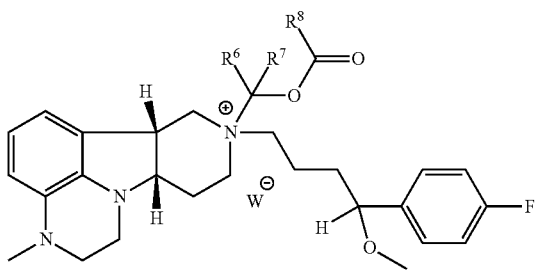

3.14 the Compound of Formula III or any of 3.1-3.12, wherein the Compound is:

Formula III

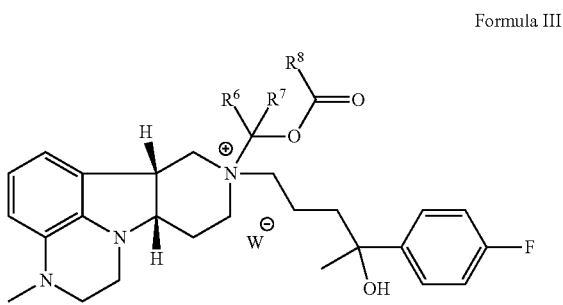

3.15 the Compound of Formula III or any of 3.12-3.14, wherein the Compound is in substantially pure diastereomeric form (i.e., substantially free from other diastereomers);

3.16 the Compound of Formula III or any of 3.1-3.15, wherein the Compound has a diasteromeric excess of greater than 70%, preferably greater than 80%, more preferably greater than 90% and most preferably greater than 95%;

3.17 the compound of Formula III or any of 3.1-3.16, wherein R$^8$, R$^a$, R$^b$, R$^c$, R$^d$, R$^e$, R$^6$, R$^7$ and W$^-$ are independently as described in any of formulae 1.15-1.32;

3.18 the compound of Formula III or any of formulae 3.1-3.17, wherein the compound is in substantially pure diastereomeric form (i.e., substantially free from other diastereomers);

3.19 the compound of Formula III or any of formulae 3.1-3.18, wherein the compound has a diasteromeric excess of greater than 70%, preferably greater than 80%, more preferably greater than 90% and most preferably greater than 95%.

In the fourth aspect, the invention provides a compound of Formula IV:

Formula IV

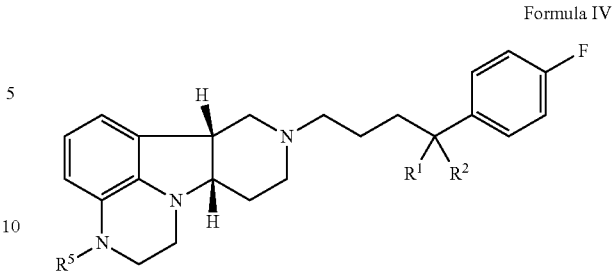

wherein:
R$^5$ is —C(O)—O—C(R$^a$)(R$^b$)(R$^c$) or —C(R$^6$)(R$^7$)—O—C(O)—R$^8$;
R$^8$ is —C(R$^a$)(R$^b$)(R$^e$), —O—C(R$^a$)(R$^b$)(R$^e$) or —N(R$^d$)(R$^e$);
R$^a$, R$^b$ and R$^c$ are independently H or C$_{1-24}$alkyl;
R$^d$ and R$^e$ are independently H or C$_{1-24}$alkyl;
R$^6$ and R$^7$ are independently H or C$_{1-6}$alkyl;
R$^1$ is H or C$_{1-6}$alkyl (e.g., methyl);
R$^2$ is H or OR$^3$ wherein R$^3$ is H, C$_{1-6}$alkyl (e.g., methyl) or —C(O)—C$_{1-21}$alkyl; provided that R$^1$ and R$^2$ are not both H, R$^1$ and R$^3$ are not both H, and when R$^3$ is —C(O)—C$_{1-21}$alkyl, R$^1$ is C$_{1-6}$alkyl (e.g., methyl), in free, salt or prodrug form.

In a particular embodiment, the compound of Formula IV is a compound wherein:
R$^5$ is —C(O)—O—C(R$^a$)(R$^b$)(R$^c$) or —C(R$^6$)(R$^7$)—O—C(O)—R$^8$;
R$^8$ is —C(R$^a$)((R$^b$)(R$^c$), —O—C(R$^a$)((R$^b$)(R$^c$) or —N(R$^d$)(R$^e$);
R$^a$, R$^b$ and R$^c$ are independently H or C$_{1-24}$alkyl;
R$^d$ and R$^e$ are independently H or C$_{1-24}$alkyl;
R$^6$ and R$^7$ are independently H or C$_{1-6}$alkyl;
R$^1$ is H or C$_{1-6}$alkyl (e.g., methyl);
R$^2$ is H or OR$^3$ wherein R$^3$ is H or C$_{1-6}$alkyl (e.g., methyl); provided that R$^1$ and R$^2$ are not both H, and R$^1$ and R$^3$ are not both H, in free, salt or prodrug form.

In a further embodiment of the fourth aspect, the invention provides a compound of Formula IV as hereinbefore described as follows:

4.1. the compound of Formula IV, wherein R$^8$, R$^a$, R$^b$, R$^c$, R$^d$, R$^e$, R$^6$, R$^7$, R$^5$ and are independently as described in any of formulae 2.10-2.28;

4.2. the compound of Formula IV or 4.1, wherein R$^1$, R$^2$ and R$^3$ are independently as described in any of formulae 3.1-3.12;

4.3. the compound of Formula IV or any of formulae 4.1-4.2, wherein the compound is in substantially pure diastereomeric form (i.e., substantially free from other diastereomers);

4.4. the compound of Formula IV or any of formulae 4.1-4.2, wherein the compound has a diasteromeric excess of greater than 70%, preferably greater than 80%, more preferably greater than 90% and most preferably greater than 95%.

in free, salt or prodrug form.

The compounds of the present invention, e.g., the compounds of Formula I, I(a), I(b) or any of formulae 1.1-1.38 as hereinbefore described, Formula II, II(a), II(b) or any of formulae 2.1-2.31, as hereinbefore described; or a compound of Formula III or any of formulae 3.1-3.19 as hereinbefore described; and a compound of Formula IV or any of formulae 4.1-4.4 as hereinbefore described, are useful as prodrugs, which may be cleaved to release the active compounds. Wherein $R^4$ of the compounds of Formula I et seq. and Formula II et seq. is —C(O)—$C_{1-21}$alkyl, or $R^3$ of the compounds of Formula III et seq. and Formula IV et seq. is —C(O)—$C_{1-21}$alkyl, these compounds may exists as a mix prodrug wherein the —C(O)—$C_{1-21}$alkyl or $R^5$ or —C($R^6$)($R^7$)—OC(O)$R^9$ may be independently cleaved off. Upon cleavage, the compounds of Formula I et seq. will release the active compound:

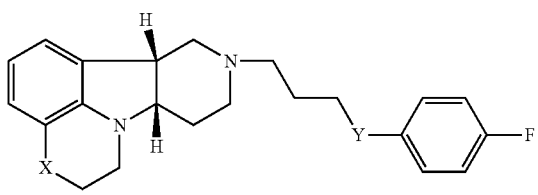

wherein X is —N(H)—, —N($C_{1-6}$alkyl)- or —O—; Y is —C(O)—, —O— or —C(H)(O$R^4$)—; and $R^4$ is H. Similarly, the compounds of Formula II et seq. will be cleaved to release the active compound:

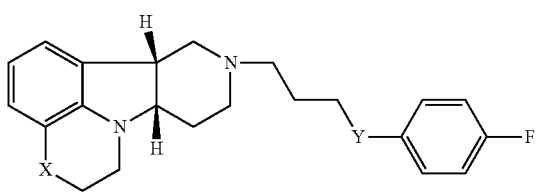

wherein X is —N(H)—; Y is —C(O)—, —O— or —C(H)(O$R^4$)—; and $R^4$ is H. The compound of Formula III et seq. will be cleaved to release the active compound:

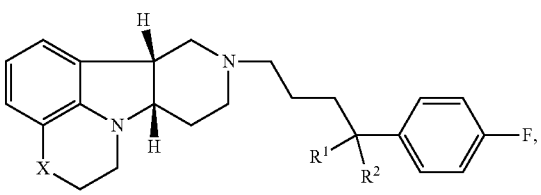

wherein X is —N(H)—, —N($C_{1-6}$alkyl)- or —O—; $R^1$ is H or $C_{1-6}$alkyl (e.g., methyl); and $R^2$ is H or O$R^3$ wherein $R^3$ is H, provided that $R^1$ and $R^2$ are not both H, and $R^1$ and $R^3$ are not both H. The compound of Formula IV et seq. will be cleaved to release the active compound:

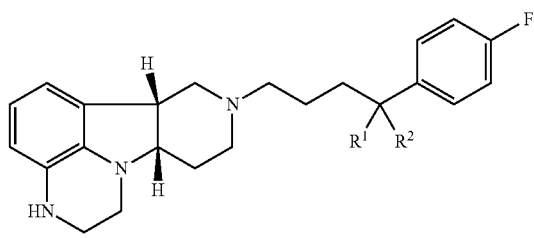

wherein $R^1$ is H or $C_{1-6}$alkyl (e.g., methyl); $R^2$ is H or O$R^3$ wherein $R^3$ is H; provided that $R^1$ and $R^2$ are not both H, and IV and $R^3$ are not both H. The compounds of the invention are believed to provide an extended release of the active compound.

In the fifth aspect, the invention provides a pharmaceutical composition comprising a compound of the current invention as hereinbefore described, in admixture with a pharmaceutically acceptable diluent or carrier. Therefore, in a further embodiment of the fifth aspect, the invention provides the following:

5.1. A Pharmaceutical Composition comprising the compound of Formula I, I(a), I(b) or any of formulae 1.1-1.38 as hereinbefore described, in admixture with a pharmaceutically acceptable diluent or carrier (Pharmaceutical Composition 5.1);

5.2. A Pharmaceutical Composition comprising the compound of Formula II, II(a), II(b) or any of formulae 2.1-2.31, in free or pharmaceutically acceptable salt form as hereinbefore described, in admixture with a pharmaceutically acceptable diluent or carrier (Pharmaceutical Composition 5.2);

5.3. A Pharmaceutical Composition comprising the compound of Formula III or any of formulae 3.1-3.19 as hereinbefore described, in admixture with a pharmaceutically acceptable diluent or carrier (Pharmaceutical Composition 5.3);

5.4. A Pharmaceutical Composition comprising the compound of Formula IV or any of formulae 4.1-4.4 as hereinbefore described, in free or pharmaceutically acceptable salt form, in admixture with a pharmaceutically acceptable diluent or carrier (Pharmaceutical Composition 5.4);

5.5. A Pharmaceutical Composition comprising the compound of Formula Q:

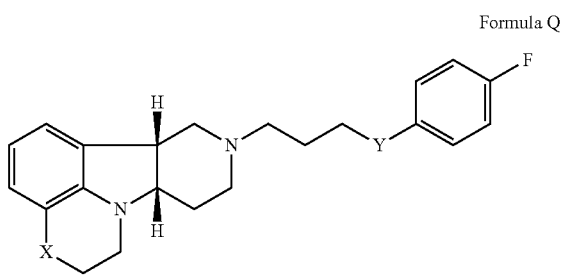

Formula Q wherein X is —N(H)—, —N(CH$_3$)— or —O—; and Y is —C(=O), —O— or —C(H)(OH), in free or pharmaceutically acceptable salt form, in admixture with a pharmaceutically acceptable diluent or carrier (Pharmaceutical Composition 5.5).

In a further embodiment of the fifth aspect, the invention provides the Pharmaceutical Composition of any of formulae 5.1-5.5, which comprises a vehicle comprising an optional viscosity enhancing agent. The drug substance or their prodrugs (e.g., the compound disclosed herein) can be dispersed or suspended in the vehicle. The vehicle is preferably an aqueous vehicle which suspends the compounds of the invention disclosed herein. Preferably, the vehicle contains a viscosity enhancing agent. Preferably, these pharmaceutical compositions comprising an optional viscosity enhancing agent are free or substantially free of sustained release matrices such as macromolecules like albumin present in major amounts (e.g., 50% by weight or more of total solids), and polymeric matrix like poly lactide-co-glycolide polymers. It is believed that these pharmaceutical compositions will provide an extended release profile similar to that obtained by the injection of a poly lactide-co-glycolide microsphere formulation containing the active agent.

Viscous vehicles useful for the fifth aspect can have, for example, a viscosity of at least 20 cp at 20° C. In other embodiments, the fluid phase of the suspension has a viscosity at 20° C. of at least about 30 cp, 40 cp, 50 cp, and 60 cp. The viscosity can be achieved by adding a viscosity enhancing agent, such as a carboxymethyl cellulose, such as sodium carboxy methylcellulose. The pharmaceutical composition comprising a viscosity enhancing agent such as a carboxy methylcellulose provides an extended or sustained release for the compound described herein. In one embodiment, the injection vehicle comprises at least about 1% by volume sodium carboxymethyl cellulose, preferably about 3% by volume carboxymethyl cellulose. See U.S. Pat. Nos. 8,338,427 and 8,338,428, the contents of each of which are incorporated by reference in their entirety. In one embodiment, the invention provides the Pharmaceutical Composition 5.5, wherein the compound of Formula Q is a compound wherein X is —N(CH$_3$)— and Y is —C(=O), in free or pharmaceutically acceptable salt form. In another embodiment, the invention provides the Pharmaceutical Composition 5.5, wherein the compound of Formula Q is a compound wherein X is —N(CH$_3$)— and Y is —C(=O), in free or pharmaceutically acceptable salt form, and the viscosity enhancing agent is sodium carboxy methylcellulose.

In the sixth aspect, the invention provides a pharmaceutical composition, e.g., for sustained or delayed release, e.g., depot, formulation, comprising (i) the compound as described in any of formulae 6.1-6.5; and (ii) a polymeric matrix:

6.1. the compound of Formula I, I(a), I(b) or any of formulae 1.1-1.38 as hereinbefore described (Pharmaceutical Composition 6.1);
6.2. the compound of Formula II, II(a), II(b) or any of formulae 2.1-2.31, in free or pharmaceutically acceptable salt form as hereinbefore described (Pharmaceutical Composition 6.2);
6.3. the compound of Formula III or any of formulae 3.1-3.19 as hereinbefore described (Pharmaceutical Composition 6.3);
6.4. the compound of Formula IV or any of formulae 4.1-4.4 as hereinbefore described, in free or pharmaceutically acceptable salt form (Pharmaceutical Composition 6.4); or
6.5. the compound of Formula Q:

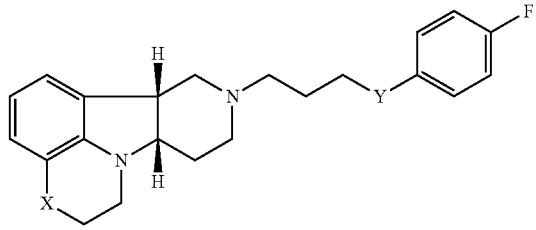

Formula Q wherein X is —N(H)—, —N(CH$_3$)— or —O—; and Y is —C(=O), —O— or —C(H)(OH), in free or pharmaceutically acceptable salt form, in admixture with a pharmaceutically acceptable diluent or carrier (Pharmaceutical Composition 6.5).

In a further embodiment, the polymeric matrix comprises standard polymers used in depot formulations such as polymers selected from apolyester of a hydroxyfatty acid and derivatives thereof, or a polymer of an alkyl alpha-cyano-acrylate, a polyalkylene oxalate, a polyortho ester, a polycarbonate, a polyortho-carbonate, a polyamino acid, a hyaluronic acid ester, and mixtures thereof. In a further embodiment, the polymer is selected from a group consisting of polylactide, poly d,l-lactide, poly glycolide, PLGA 50:50, PLGA 85:15 and PLGA 90:10 polymer. In another embodiment, the polymer is selected from poly(glycolic acid), poly-D,L-lactic acid, poly-L-lactic acid, copolymers of the foregoing, poly(aliphatic carboxylic acids), copolyoxalates, polycaprolactone, polydioxonone, poly(ortho carbonates), poly(acetals), poly(lactic acid-caprolactone), polyorthoesters, poly(glycolic acid-caprolactone), polyanhydrides, and natural polymers including albumin, casein, and waxes, such as, glycerol mono- and distearate, and the like. In a preferred embodiment, the polymeric matrix comprises poly(d,l-lactide-co-glycolide). For example, the Pharmaceutical Composition of any of formulae 6.1-6.5 wherein said compound is dissolved or dispersed in a polymeric matrix which comprises a poly(d,l-lactide-co-glycolide). Any of Pharmaceutical Compositions of formulae 6.1-6.5 as hereinbefore described may be in admixture with a pharmaceutically acceptable diluent or carrier.

The pharmaceutical compositions of any of formulae 5.1-5.5 or the pharmaceutical composition of any of formulae 6.1-6.5 are particularly useful for sustained or delayed release, wherein the compound is released upon degradation of the polymeric matrix and/or the prodrug. Therefore, these compositions may be formulated for controlled- and/or sustained-release of the active compounds as described above over a period of up to 180 days, e.g., from about 7 to about 14 to about 30 to about 180 days. For example, the polymeric matrix may degrade and release the compounds disclosed herein over a period of about 7, about 14, about 30, about 60 or about 90 days. In another example, the polymeric matrix may degrade and release the compounds disclosed herein over a period of about 120, or about 180 days. Therefore, in one embodiment, the Pharmaceutical Composition of any of formulae 5.1-5.5 or 6.1-6.5 releases the compound over a period of up to 180 days, about 120 days, about 90 days, about 60 days, about 30 days, about 14 days or about 7 days.

In still another further embodiment, the Pharmaceutical Compositions of the Invention (e.g., any of formulae 5.1-5.5 and any of formulae 6.1-6.5) are formulated for administration by injection. In another embodiment, the Pharmaceutical Compositions of the Invention (e.g., Pharmaceutical Composition of any of formulae 5.1-5.5 or 6.1-6.5) may be formulated for oral administration.

In the seventh aspect, the invention provides the compound as hereinbefore described in any of formulae 5.1-5.5 or 6.1-6.5, in an osmotic controlled release oral delivery system (OROS). In a particular embodiment of the seventh aspect, the invention provides a device comprising (a) a gelatin capsule containing the compound described in any of formulae 5.1-5.5 or 6.1-6.5; (b) a multilayer wall superposed on the gelatin capsule comprising, in outward order from the capsule: (i) a barrier layer, (ii) an expandable layer, and (iii) a semipermeable layer; and (c) and orifice formed or formable through the wall. (Composition P.1) Osmotic controlled release oral delivery system is described in WO 2000/35419 and EP 1 539 115 (U.S. Pub. No. 2009/0202631), the contents of each of which applications are incorporated by reference in their entirety.

In another embodiment of the seventh aspect, the invention provides a composition comprising a gelatin capsule containing a liquid, the compound as described in any of formulae 5.1-5.5 or 6.1-6.5, the gelatin capsule being surrounded by a composite wall comprising a barrier layer contacting the external surface of the gelatin capsule, an expandable layer contacting the barrier layer, a semi-permeable layer encompassing the expandable layer, and an exit orifice formed or formable in the wall. (Composition P.2)

In still another embodiment of the seventh aspect, the invention provides a composition comprising a gelatin capsule containing a liquid, the compound as described in any of formulae 5.1-5.5 or 6.1-6.5, the gelatin capsule being surrounded by a composite wall comprising a barrier layer contacting the external surface of the gelatin capsule, an expandable layer contacting the barrier layer, a semipermeable layer encompassing the expandable layer, and an exit orifice formed or formable in the wall, wherein the barrier layer forms a seal between the expandable layer and the environment at the exit orifice. (Composition P.3)

In still another embodiment of the seventh aspect, the invention provides a composition comprising a gelatin capsule containing a liquid, the compound as described in any of formulae 5.1-5.5 or 6.1-6.5, the gelatin capsule being surrounded by a barrier layer contacting the external surface of the gelatin capsule, an expandable layer contacting a portion of the barrier layer, a semi-permeable layer encompassing at least the expandable layer, and an exit orifice formed or formable in the dosage form extending from the external surface of the gelatin capsule to the environment of use. (Composition P.4). The expandable layer may be formed in one or more discrete sections, such as for example, two sections located on opposing sides or ends of the gelatin capsule.

In a particular embodiment of the seventh aspect, the compound in the Osmotic-controlled Release Oral delivery System (i.e., in Composition P.1-P.4) is in a liquid formulation, which formulation may be neat, liquid active agent, liquid active agent in a solution, suspension, emulsion or self-emulsifying composition or the like.

Further information on Osmotic-controlled Release Oral delivery System composition including characteristics of the gelatin capsule, barrier layer, an expandable layer, a semi-permeable layer; and orifice may be found in WO 2000/35419, the contents of which are incorporated by reference in their entirety.

Other Osmotic-controlled Release Oral delivery System useful for the compounds or the Pharmaceutical Compositions of the Invention may be found in EP 1 539 115 (U.S. Pub. No. 2009/0202631), the contents of which are incorporated by reference in their entirety. Therefore, in another embodiment of the seventh aspect, the invention provides a composition or device comprising (a) two or more layers, said two or more layers comprising a first layer and a second layer, said first layer comprises the compound as described in any of formulae 5.1-5.5 or 6.1-6.5, or a Pharmaceutical Composition as herein before described said second layer comprises a polymer; (b) an outer wall surrounding said two or more layers; and (c) an orifice in said outer wall. (Composition P.5)

Composition P.5 preferably utilizes a semi-permeable membrane surrounding a three-layer-core: in these embodiments the first layer is referred to as a first drug layer and contains low amounts of drug (e.g., the compounds disclosed herein) and an osmotic agent such as salt, the middle layer referred to as the second drug layer contains higher amounts of drug, excipients and no salt; and the third layer referred to as the push layer contains osmotic agents and no drug. At least one orifice is drilled through the membrane on the first drug layer end of the capsule-shaped tablet. (Composition P.6)

Composition P.5 or P.6 may comprise a membrane defining a compartment, the membrane surrounding an inner protective subcoat, at least one exit orifice formed or formable therein and at least a portion of the membrane being semi-permeable; an expandable layer located within the compartment remote from the exit orifice and in fluid communication with the semi-permeable portion of the membrane; a first drug layer located adjacent the exit orifice; and a second drug layer located within the compartment between the first drug layer and the expandable layer, the drug layers comprising the compound of the Invention in free or pharmaceutically acceptable salt thereof. Depending upon the relative viscosity of the first drug layer and second drug layer, different release profiles are obtained. It is important to identify the optimum viscosity for each layer. In the present invention, viscosity is modulated by addition of salt, sodium chloride. The delivery profile from the core is dependent on the weight, formulation and thickness of each of the drug layers. (Composition P.7)

In a particular embodiment, the invention provides Composition P.7 wherein the first drug layer comprising salt and the second drug layer containing no salt. Composition P.5-P.7 may optionally comprise a flow-promoting layer between the membrane and the drug layers.

Compositions P.1-P.7 will generally be referred to as Osmotic-controlled Release Oral delivery System Composition.

In the eighth aspect, the invention provides a method (Method I) for the treatment or prophylaxis of a central nervous system disorder, comprising administering to a patient in need thereof an effective amount of:
 8.1. a compound of Formula I, I(a), I(b) or any of formulae 1.1-1.38 as hereinbefore described;
 8.2. a compound of Formula II, II(a), II(b) or any of formulae 2.1-2.31, in free or pharmaceutically acceptable salt form as hereinbefore described;
 8.3. a compound of Formula III or any of formulae 3.1-3.19 as hereinbefore described;
 8.4. a compound of Formula IV or any of formulae 4.1-4.4 as hereinbefore described, in free or pharmaceutically acceptable salt form;
 8.5. a Pharmaceutical Composition as described in formula 5.1;
 8.6. a Pharmaceutical Composition as described in formula 5.2;
 8.7. a Pharmaceutical Composition as described in formula 5.3;
 8.8. a Pharmaceutical Composition as described in formula 5.4;
 8.9. a Pharmaceutical Composition as described in formula 5.5;
 8.10. a Pharmaceutical Composition of any of formulae 6.1-6.5; or
 8.11. Composition of any of formulae P.1-P.7 as hereinbefore described;

In a further embodiment of the eighth aspect, the invention provides Method I or any of Formulae 8.1-8.11, wherein the method is further as described in the following formulae:
 8.12. Method I or any of Formulae 8.1-8.11, wherein the central nervous system disorder is a disorder selected from a group consisting of obesity, anxiety, depression (for example refractory depression and MDD), psychosis, schizophrenia, sleep disorders (particularly sleep disorders associated with schizophrenia and other psychiatric and neurological diseases), sexual disorders, migraine, conditions associated with cephalic pain, social phobias, agitation in dementia (e.g., agitation in Alzheimer's disease), agitation in autism and related autistic disorders, and gastrointestinal disorders such as dysfunction of the gastrointestinal tract motility;

8.13. Method I or any of Formulae 8.1-8.11, wherein the central nervous system disorder is a disorder involving serotonin 5-HT$_2$A, dopamine D$_2$ receptor system and/or serotonin reuptake transporter (SERT) pathways as similarly described in WO/2009/145900, the contents of which are herein incorporated by reference in their entirety;

8.14. Method I or any of Formulae 8.1-8.11, wherein the central nervous system disorder is a disorder involving serotonin reuptake transporter (SERT) pathways;

8.15. Method I or any of Formulae 8.1-8.11, wherein the central nervous system disorder is a disorder selected from the following: (i) psychosis, e.g., schizophrenia, in a patient suffering from depression; (2) depression in a patient suffering from psychosis, e.g., schizophrenia; (3) mood disorders associated with psychosis, e.g., schizophrenia or Parkinson's disease; and (4) sleep disorders associated with psychosis, e.g., schizophrenia or Parkinson's disease; (5) depression; (6) anxiety; (7) post-traumatic stress disorder; or (8) impulse control disorder, e.g., intermittent explosive disorder, e.g., in patients suffering from psychosis (e.g., schizophrenia) or dementia;

8.16. Method I or any of Formulae 8.1-8.12, wherein the central nervous system disorder is a disorder selected from the following: (i) psychosis, e.g., schizophrenia, in a patient suffering from depression; (2) depression in a patient suffering from psychosis, e.g., schizophrenia; (3) mood disorders associated with psychosis, e.g., schizophrenia or Parkinson's disease; and (4) sleep disorders associated with psychosis, e.g., schizophrenia or Parkinson's disease;

8.17. Method I or any of Formulae 8.1-8.13, wherein the central nervous system disorder is psychosis, e.g., schizophrenia and said patient is a patient suffering from depression;

8.18. Method I or any of Formulae 8.1-8.16, wherein said patient is unable to tolerate the side effects of convention antipsychotic drugs, e.g., chlorpromazine, haloperidol droperidol, fluphenazine, loxapine, mesoridazine molidone, perphenazine, pimozide, prochlorperazine promazine, thioridazine, thiothixene, trifluoperazine, clozapine, aripiparazole, olanzapine, quetiapine, risperidone and ziprasidone;

8.19. Method I or any of Formulae 8.1-8.17, wherein said patient is unable to tolerate the side effects of convention antipsychotic drugs, e.g., haloperidol, aripiparazole, clozapine, olanzapine, quetiapine, risperidone, and zipasidone;

8.20. Method I or any of Formulae 8.1-8.18, wherein said disorder is depression and said patient is a patient suffering from psychosis, e.g., schizophrenia, or Parkinson's disease;

8.21. Method I or any of Formulae 8.1-8.13, wherein said disorder is sleep disorder and said patient is suffering from depression;

8.22. Method I or any of 8.1-8.13, wherein said one or more disorders is sleep disorder and said patient is suffering from psychosis, e.g., schizophrenia;

8.23. Method I or any of 8.1-8.13, wherein said one or more disorders is sleep disorder and said patient is suffering from Parkinson's disease;

8.24. Method I or any of 8.1-8.13, wherein said one or more disorders is sleep disorder and said patient is suffering from depression and psychosis, e.g., schizophrenia, or Parkinson's disease;

8.25. Any of the foregoing methods, wherein the effective amount is 1 mg-1000 mg, preferably 2.5 mg-50 mg, in free or pharmaceutically acceptable salt, non-prodrug form, per day;

8.26. Any of the foregoing methods, wherein the effective amount is 1 mg-100 mg per day, preferably 2.5 mg-50 mg, in free or pharmaceutically acceptable salt, non-prodrug form, per day;

8.27. Any of the foregoing methods wherein a condition to be treated is dyskinesia, e.g. in a patient receiving dopaminergic medications, e.g., medications selected from levodopa and levodopa adjuncts (carbidopa, COMT inhibitors, MAO-B inhibitors), dopamine agonists, and anticholinergics, e.g., levodopa;

8.28. Any of the foregoing methods wherein the patient suffers from Parkinson's disease;

8.29. Any of the foregoing methods wherein the patient does not respond to a selective serotonin re-uptake inhibitor, e.g. selected from one or more of citalopram (Celexa, Cipramil, Cipram, Dalsan, Recital, Emocal, Sepram, Seropram, Citox, Cital); dapoxetine (Priligy); escitalopram (Lexapro, Cipralex, Seroplex, Esertia); fluoxetine (Depex, Prozac, Fontex, Seromex, Seronil, Sarafem, Ladose, Motivest, Flutop, Fluctin (EUR), Fluox (NZ), Depress (UZB), Lovan (AUS), Prodep (IND)); fluvoxamine (Luvox, Fevarin, Faverin, Dumyrox, Favoxil, Movox); indalpine (Upstene); paroxetine (Paxil, Seroxat, Sereupin, Aropax, Deroxat, Divarius, Rexetin, Xetanor, Paroxat, Loxamine, Deparoc); sertraline (Zoloft, Lustral, Serlain, Asentra); vilazodone (Viibryd); or zimelidine (Zelmid, Normud).

8.30. Any of the foregoing methods wherein the patients is also receiving a selective serotonin re-uptake inhibitor, e.g. selected from one or more of citalopram (Celexa, Cipramil, Cipram, Dalsan, Recital, Emocal, Sepram, Seropram, Citox, Cital); dapoxetine (Priligy); escitalopram (Lexapro, Cipralex, Seroplex, Esertia); fluoxetine (Depex, Prozac, Fontex, Seromex, Seronil, Sarafem, Ladose, Motivest, Flutop, Fluctin (EUR), Fluox (NZ), Depress (UZB), Lovan (AUS), Prodep (IND)); fluvoxamine (Luvox, Fevarin, Faverin, Dumyrox, Favoxil, Movox); indalpine (Upstene); paroxetine (Paxil, Seroxat, Sereupin, Aropax, Deroxat, Divarius, Rexetin, Xetanor, Paroxat, Loxamine, Deparoc); sertraline (Zoloft, Lustral, Serlain, Asentra); vilazodone (Viibryd); or zimelidine (Zelmid, Normud).

In still another preferred embodiment of the eighth aspect, the invention provides Method I or any of 8.1-8.30, wherein the Compounds or Compositions of the Invention as hereinbefore described are administered for controlled- and/or sustained-release of the active compounds of the invention over a period of from about 7 days, about 14 days, about 30 to about 180 days, preferably over the period of about 30, about 60 or about 90 days. Controlled- and/or sustained-release is particularly useful for circumventing premature discontinuation of therapy, particularly for antipsychotic drug therapy where non-compliance or non-adherence to medication regimes is a common occurrence.

In another embodiment of the eighth aspect, the invention provides methods for the prophylaxis or treatment of one or more disorders associated with dementia, e.g., disorders associated with mild cognition impairment and dementing illnesses including senile dementia, Alzheimer's disease, Pick's disease, frontotemporal dementia, parasupranuclear palsy, dementia with Lewy bodies and vascular dementia comprising administering to a patient in need thereof, a therapeutically effective amount of a compound as described in any of formulae 8.1-8.11 (Method III).

In a further embodiment, the invention provides Method III as follows:

- 8.31. Method III, wherein the disorders associated with dementia are disorders associated with mild cognition impairment and dementing illnesses including senile dementia, Alzheimer's disease, Pick's disease, frontotemporal dementia, parasupranculear palsy, dementia with Lewy bodies and vascular dementia; 8.32. Method III or 8.31, wherein the disorders associated with dementia are disorders associated with senile dementia, Alzheimer's disease, Pick's disease, frontotemporal dementia, parasupranculear palsy, dementia with Lewy bodies and vascular dementia;
- 8.33. Method III or 8.31, wherein the disorders associated with dementia are disorders associated with Alzheimer's disease;
- 8.34. Method III or 8.31, wherein the disorders associated with dementia are disorders associated with mild cognition impairment;
- 8.35. Method III or any of 8.31-8.34, wherein the disorder associated dementia to be treated is selected from the group consisting of (1) behavioral or mood disorders such as agitation/irritation, aggressive/assaultive behavior, anger, physical or emotional outbursts; (2) psychosis; (3) depression; and (4) sleep disorders in patients suffering from dementia, particularly Alzheimer's disease;
- 8.36. Method III or any of 8.35-8.34, wherein the disorder to be treated is psychosis in a patient with dementia, particularly Alzheimer's disease;
- 8.37. Method III or any of 8.35-8.34, wherein the disorder to be treated is depression in a patient with dementia, particularly Alzheimer's disease;
- 8.38. Method III or any of 8.35-8.34, wherein the dosage of the Compound of the invention is 10-100 mg, in free or pharmaceutically acceptable salt, non-prodrug form, per day;
- 8.39. Method III or any of the formulae above, wherein the disorder to be treated is behavioral or mood disorders such as agitation/irritation, aggressive/assaultive behavior, anger, physical or emotional outbursts in a patient with dementia, particularly Alzheimer's disease;
- 8.40. Method III or any of the formulae above, wherein the disorder to be treated is sleep disorders in a patient with dementia, particularly Alzheimer's disease;
- 8.41. Method III or any of the formulae above, wherein the disorder to be treated is sleep maintenance insomnia, frequent awakenings, and waking up feeling unrefreshed in a patient with dementia, particularly Alzheimer's disease;
- 8.42. Method III or any of the formulae above, wherein the disorder to be treated is sleep maintenance insomnia in a patient with dementia, particularly Alzheimer's disease;
- 8.43. Method III or any of the formulae above, wherein the disorder to be treated is advanced sleep-phase syndrome in a patient with dementia, particularly Alzheimer's disease;
- 8.44. Method III or any of the formulae above, wherein the disorder to be treated is delayed sleep-phase syndrome in a patient with dementia, particularly Alzheimer's disease;
- 8.45. Method III or any of the formulae above, wherein the dosage of the Compound of the invention is 1-10 mg per day;
- 8.46. Method III or any of the formulae above, further comprises administering one or more therapeutic agents useful for the prophylaxis or treatment of dementia, particularly Alzheimer's disease;
- 8.47. Method III or any of the formulae above, wherein the therapeutic agent useful for the prophylaxis or treatment of dementia, particularly Alzheimer's disease is a cholinesterase inhibitor (e.g., acetylcholinesterase inhibitor) or an N-Methyl D-Asparate (NMDA) receptor antagonist, in free or pharmaceutically acceptable salt form;
- 8.48. Method III or any of the formulae above, wherein the cholinesterase inhibitor (e.g., acetylcholinesterase inhibitor) is selected from the group consisting of Tacrine, rivastigmine (Exelon), donepezil (Aricept), and galantamine (Razadyne, formerly called Reminyl)) in free or pharmaceutically acceptable salt form;
- 8.49. Method III or any of the formulae above, wherein the cholinesterase inhibitor (e.g., acetylcholinesterase inhibitor) is donepezil in free or pharmaceutically acceptable salt form;
- 8.50. Method III or any of the formulae above, wherein the NMDA receptor antagonist is memantine in free or pharmaceutically acceptable salt form;
- 8.51. Method III or any of the formulae above, wherein the therapeutic agent useful for the prophylaxis or treatment of dementia, particularly Alzheimer's disease is a combination of a cholinesterase inhibitor (e.g., acetylcholinesterase inhibitor) and an N-Methyl D-Asparate (NMDA) receptor antagonist;
- 8.52. Method III or any of the formulae above, wherein the one or more therapeutic agent(s) useful for the prophylaxis or treatment of dementia, particularly Alzheimer's disease or symptoms thereof is a combination of donepezil and memantine in free or pharmaceutically acceptable salt form.

In the ninth aspect, the invention provides a method (Method II) for the prophylaxis or treatment one or more sleep disorders comprising administering to a patient in need thereof an effective amount of a compound as described in the following formulae:

- 9.1 a compound of Formula I, I(a), I(b) or any of formulae 1.1-1.37 as hereinbefore described;
- 9.2 a compound of Formula II, II(a), II(b) or any of formulae 2.1-2.31, in free or pharmaceutically acceptable salt form as hereinbefore described;
- 9.3 a compound of Formula III or any of formulae 3.1-3.19 as hereinbefore described;
- 9.4 a compound of Formula IV or any of formulae 4.1-4.4 as hereinbefore described, in free or pharmaceutically acceptable salt form;
- 9.5 a Pharmaceutical Composition as described in formula 5.1;
- 9.6 a Pharmaceutical Composition as described in formula 5.2;
- 9.7 a Pharmaceutical Composition as described in formula 5.3;
- 9.8 a Pharmaceutical Composition as described in formula 5.4;

9.9 a Pharmaceutical Composition as described in formula 5.5;
9.10 a Pharmaceutical Composition of any of formulae 6.1-6.5; or
9.11 Composition of any of formulae P.1-P.7 as hereinbefore described;

In a further embodiment of the ninth aspect, the invention provides Method II, 9.1-9.11, wherein the sleep disorder includes sleep maintenance insomnia, frequent awakenings, and waking up feeling unrefreshed;
9.12 Any of the foregoing methods, wherein the sleep disorder is sleep maintenance insomnia;
9.13 Any of the foregoing methods, wherein the effective amount is 1 mg-10 mg, e.g., 1 mg-5 mg, preferably 2.5-5 mg, in free or pharmaceutically acceptable salt, non-prodrug form, per day;
9.14 Any of the foregoing methods, wherein the effective amount is 2.5 mg or 5 mg, in free or pharmaceutically acceptable salt, non-prodrug form, per day;
9.15 Any of the foregoing methods wherein the sleep disorder is in a patient suffering from or at risk of dyskinesia, e.g., a patient receiving dopaminergic medications, e.g., selected from levodopa and levodopa adjuncts (carbidopa, COMT inhibitors, MAO-B inhibitors), dopamine agonists, and anticholinergics, e.g., receiving levodopa;
9.16 Any of the foregoing methods wherein the patient suffers from Parkinson's disease.

The compound of Formula Q as hereinbefore described and the compounds of the Invention, upon conversion to the compound of Formula Q, or the active compounds as hereinbefore described, provides effective treatment of 5-HT2A, SERT and/or $D_2$ receptor related disorders without or with minimal extrapyramidal side effects as similarly disclosed and claimed in WO 2009/145900, the contents of which are incorporated by reference in their entirety. Therefore, the compounds of the Invention, the Pharmaceutical Compositions of the Invention or the Depot formulation (Compositions of any of formulae 5.1-5.5 or 6.1-6.5) may be used in combination with a second therapeutic agent, particularly at lower dosages than when the individual agents are used as a monotherapy so as to enhance the therapeutic activities of the combined agents without causing the undesirable side effects commonly occur in conventional monotherapy. Therefore, the compounds of the Invention may be simultaneously, sequentially, or contemporaneously administered with other anti-depressant, anti-psychotic, other hypnotic agents, and/or agents use to treat Parkinson's disease or mood disorders. In another example, side effects may be reduced or minimized by administering an effective amount of a compound of the Invention in combination with one or more second therapeutic agents in free or salt form, wherein the dosages of (i) the second therapeutic agent(s) or (ii) both compound of the Invention and the second therapeutic agents, are lower than if the agents/compounds are administered as a monotherapy. In a particular embodiment, the compounds of the Invention are useful to treat dyskinesia in a patient receiving dopaminergic medications, e.g., selected from levodopa and levodopa adjuncts (carbidopa, COMT inhibitors, MAO-B inhibitors), dopamine agonists, and anticholinergics, e.g., such as are used in the treatment of Parkinson's disease.

Therefore, in the tenth aspect, the current invention provides Method I or III, e.g., or any of formulae 8.1-8.52, or Method II or any of 9.1-9.16, further comprises one or more therapeutic agents selected from compounds that modulate GABA activity (e.g., enhances the activity and facilitates GABA transmission), a GABA-B agonist, a 5-HT modulator (e.g., a 5-HT1a agonist, a 5-HT$_{2A}$ antagonist, a 5-HT2a inverse agonist, etc.), a melatonin agonist, an ion channel modulator (e.g., blocker), a serotonin-2 antagonist/reuptake inhibitor (SARIs), an orexin receptor antagonist, an H3 agonist or antagonist, a noradrenergic agonist or antagonist, a galanin agonist, a CRH antagonist, human growth hormone, a growth hormone agonist, estrogen, an estrogen agonist, a neurokinin-1 drug, an anti-depressant, and an antipsychotic agent, e.g., an atypical antipsychotic agent, in free or pharmaceutically acceptable salt form (Method I-A, II-A, III-A, respectively).

In a further embodiment of the tenth aspect, the invention provides Method I-A, II-A or III-A as follows, further comprising one or more therapeutic agents.
10.1 Method I-A, II-A or III-A, wherein the therapeutic agent(s) is compounds that modulate GABA activity (e.g., enhances the activity and facilitates GABA transmission);
10.2 Method I-A, II-A or III-A or 10.1, wherein the GABA compound is selected from a group consisting of one or more of doxepin, alprazolam, bromazepam, clobazam, clonazepam, clorazepate, diazepam, flunitrazepam, fiurazepam, lorazepam, midazolam, nitrazepam, oxazepam, temazapam, triazolam, indiplon, zopiclone, eszopiclone, zaleplon, Zolpidem, gabaxadol, vigabatrin, tiagabine, EVT 201 (Evotec Pharmaceuticals) and estazolam;
10.3 Method I-A, II-A or III-A, wherein the therapeutic agent is an additional 5HT2a antagonist;
10.4 Method I-A, II-A or III-A or 10.3, wherein said additional 5HT2a antagonist is selected from one or more of ketanserin, risperidone, eplivanserin, volinanserin (Sanofi-Aventis, France), pruvanserin, MDL 100907 (Sanofi-Aventis, France), HY 10275 (Eli Lilly), APD 125 (Arena Pharmaceuticals, San Diego, Calif.), and AVE8488 (Sanofi-Aventis, France);
10.5 Method I-A, II-A or III-A, wherein the therapeutic agent is a melatonin agonist;
10.6 Method I-A, II-A or III-A or 10.5, wherein the melatonin agonist is selected from a group consisting of one or more of melatonin, ramelteon (ROZEREM®, Takeda Pharmaceuticals, Japan), VEC-162 (Vanda Pharmaceuticals, Rockville, Md.), PD-6735 (Phase II Discovery) and agomelatine;
10.7 Method I-A, II-A or III-A, wherein the therapeutic agent is an ion channel blocker;
10.8 Method I-A, II-A or III-A or 10.7, wherein said ion channel blocker is one or more of lamotrigine, gabapentin and pregabalin.
10.9 Method I-A, II-A or III-A, wherein the therapeutic agent is an orexin receptor antagonist;
10.10 Method I-A, II-A or III-A or 10.9, wherein the orexin receptor antagonist is selected from a group consisting of orexin, a 1,3-biarylurea, SB-334867-a (GlaxoSmithKline, UK), GW649868 (GlaxoSmithKline) and a benzamide derivative;
10.11 Method I-A, II-A or III-A, wherein the therapeutic agent is the serotonin-2 antagonist/reuptake inhibitor (SARI);
10.12 Method I-A, II-A or III-A or 10.11, wherein the serotonin-2 antagonist/reuptake inhibitor (SARI) is selected from a group consisting of one or more Org 50081 (Organon-Netherlands), ritanserin, nefazodone, serzone and trazodone;
10.13 Method I-A, II-A or III-A, wherein the therapeutic agent is the 5HT1a agonist;

10.14 Method I-A, II-A or III-A or 10.13, wherein the 5HT1a agonist is selected from a group consisting of one or more of repinotan, sarizotan, eptapirone, buspirone and MN-305 (MediciNova, San Diego, Calif.);

10.15 Method I-A, II-A or III-A, wherein the therapeutic agent is the neurokinin-1 drug;

10.16 Method I-A, II-A or III-A or 10.15, wherein the neurokinin-1 drug is Casopitant (GlaxoSmithKline);

10.17 Method I-A, II-A or III-A, wherein the therapeutic agent is an antipsychotic agent;

10.18 Method I-A, II-A or III-A or 10.17, wherein the antipsychotic agent is selected from a group consisting of chlorpromazine, haloperidol, droperidol, fluphenazine, loxapine, mesoridazine molidone, perphenazine, pimozide, prochlorperazine promazine, thioridazine, thiothixene, trifluoperazine, clozapine, aripiparazole, olanzapine, quetiapine, risperidone, ziprasidone and paliperidone;

10.19 Method I-A, II-A or III-A, wherein the therapeutic agent is an anti-depressant;

10.20 Method I-A, II-A or III-A or 10.19, wherein the anti-depressant is selected from amitriptyline, amoxapine, bupropion, citalopram, clomipramine, desipramine, doxepin, duloxetine, escitaloprame, fluoxetine, fluvoxamine, imipramine, isocarboxazid, maprotiline, mirtazapine, nefazodone, nortriptyline, paroxetine, phenlzine sulfate, protiptyline, sertraline, tranylcypromine, trazodone, trimipramine, and velafaxine;

10.21 Method I-A, II-A or III-A, 10.17 or 10.18, wherein the antipsychotic agent is an atypical antipsychotic agent;

10.22 Method I-A, II-A or III-A, or any of 10.17-10.21, wherein the atypical antipsychotic agent is selected from a group consisting of clozapine, aripiparazole, olanzapine, quetiapine, risperidone, ziprasidone, and paliperidone;

10.23 Method I-A, II-A or III-A, wherein the therapeutic agent is selected from any of methods 10.1-10.22, e.g., selected from a group consisting of modafinil, armodafinil, doxepin, alprazolam, bromazepam, clobazam, clonazepam, clorazepate, diazepam, flunitrazepam, flurazepam, lorazepam, midazolam, nitrazepam, oxazepam, temazepam, triazolam, indiplon, zopiclone, eszopiclone, zaleplon, Zolpidem, gabaxadol, vigabatrin, tiagabine, EVT 201 (Evotec Pharmaceuticals), estazolam, ketanserin, risperidone, eplivanserin, volinanserin (Sanofi-Aventis, France), pruvanserin, MDL 100907 (Sanofi-Aventis, France), HY 10275 (Eli Lilly), APD 125 (Arena Pharmaceuticals, San Diego, Calif.), AVE8488 (Sanofi-Aventis, France), repinotan, sarizotan, eptapirone, buspirone, MN-305 (Medici-Nova, San Diego, Calif.), melatonin, ramelteon (ROZEREM®, Takeda Pharmaceuticals, Japan), VEC-162 (Vanda Pharmaceuticals, Rockville, Md.), PD-6735 (Phase II Discovery), agomelatine, lamotrigine, gabapentin, pregabalin, orexin, a 1,3-biarylurea, SB-334867-a (GlaxoSmithKline, UK), GW649868 (GlaxoSmithKline), a benzamide derivative, Org 50081 (Organon-Netherlands), ritanserin, nefazodone, serzone, trazodone, Casopitant (GlaxoSmithKline), amitriptyline, amoxapine, bupropion, citalopram, clomipramine, desipramine, doxepin, duloxetine, escitaloprame, fluoxetine, fluvoxamine, imipramine, isocarboxazid, maprotiline, mirtazapine, nefazodone, nortriptyline, paroxetine, phenlzine sulfate, protiptyline, sertraline, tranylcypromine, trazodone, trimipramine, velafaxine, chlorpromazine, haloperidol, droperidol, fluphenazine, loxapine, mesoridazine molidone, perphenazine, pimozide, prochlorperazine promazine, thioridazine, thiothixene, trifluoperazine, clozapine, aripiparazole, olanzapine, quetiapine, risperidone, ziprasidone and paliperidone;

10.24 Method I-A, II-A or III-A wherein the therapeutic agent is an H3 agonist;

10.25 Method I-A, II-A or III-A, wherein the therapeutic agent is an H3 antagonist;

10.26 Method I-A, II-A or III-A, wherein the therapeutic agent is a noradrenergic agonist or antagonist;

10.27 Method I-A, II-A or III-A, wherein the therapeutic agent is a galanin agonist;

10.28 Method I-A, II-A or III-A, wherein the therapeutic agent is a CRH antagonist;

10.29 Method I-A, II-A or III-A, wherein the therapeutic agent is a human growth hormone;

10.30 Method I-A, II-A or III-A, wherein the therapeutic agent is a growth hormone agonist;

10.31 Method I-A, II-A or III-A, wherein the therapeutic agent is estrogen;

10.32 Method I-A, II-A or III-A, wherein the therapeutic agent is an estrogen agonist;

10.33 Method I-A, II-A or III-A, wherein the therapeutic agent is a neurokinin-1 drug;

10.34 Method I-A, II-A or III-A, wherein a therapeutic agent is combined with compounds of Formula (I) and the therapeutic agent is an anti-Parkinson agent such as L-dopa, co-careldopa, duodopa, stalova, Symmetrel, benzotropine, biperiden, bromocryiptine, entacapone, pergolide, pramipexole, procyclidine, ropinirole, selegiline and tolcapone;

10.35 Method I-A, II-A or III-A, wherein compounds of the invention may be used to treat sleep disorders, depression, pyschosis, or any combinations thereof, in patients suffering from the listed diseases and/or Parkinson's disease; 10.36 Method I-A, II-A or III-A, wherein the disorder is selected from at least one or more of psychosis, e.g., schizophrenia, depression, mood disorders, sleep disorders (e.g., sleep maintenance and/or sleep onset) or any combination of disorders thereof;

10.37 Any of the foregoing methods wherein the disorder is sleep disorder;

10.38 Any of the foregoing methods, wherein the disorder is sleep disorder associated with psychosis, e.g., schizophrenia or Parkinson's disease; in free or pharmaceutically acceptable salt form.

In the eleventh aspect of the invention, the combination of a compound of the Invention and one or more second therapeutic agents as described in Method I-A, II-A or III-A or any of 10.1-10.38, may be administered as a Pharmaceutical Composition or a Depot Composition as hereinbefore described. The combination compositions can include mixtures of the combined drugs, as well as two or more separate compositions of the drugs, which individual compositions can be, for example, co-administered together to a patient.

In a particular embodiment, Method I-A, II-A or III-A, or any of 10.1-10.38 comprises administering to a patient in need thereof, an effective amount a compound of the Invention in combination with an atypical antipsychotic agent, e.g., a compound selected from clozapine, aripiparazole, olanzapine, quetiapine, risperidone, ziprasidone, or paliperidone, in free or pharmaceutically acceptable salt form, for example wherein the dosage of the atypical antipsychotic agent is reduced and/or side effects are reduced.

In another embodiment, Method I-A, II-A or III-A, or any of 10.1-10.38 comprises administering to a patient in need thereof, an effective amount of a compound of the Invention in combination with an anti-depressant, e.g., amitriptyline, amoxapine, bupropion, citalopram, clomipramine, desipramine, doxepin, duloxetine, escitaloprame, fluoxetine, fiuvoxamine, imipramine, isocarboxazid, maprotiline, mirtazapine, nefazodone, nortriptyline, paroxetine, phenlzine sulfate, protiptyline, sertraline, tranylcypromine, trazodone, trimipramine, or velafaxine, in free or pharmaceutically acceptable salt form. Alternatively, the anti-depressant may be used as an adjunct medication in addition to the compound of the Invention.

In still another embodiment, Method I-A, II-A or III-A or any of 10.1-10.38 comprises administering to a patient in need thereof, an effective amount of a compound of the Invention in combination with a compound that modulates GABA activity, e.g., a compound selected from doxepin, alprazolam, bromazepam, clobazam, clonazepam, clorazepate, diazepam, flunitrazepam, flurazepam, lorazepam, midazolam, nitrazepam, oxazepam, temazapam, triazolam, indiplon, zopiclone, eszopiclone, zaleplon, Zolpidem, gabaxadol, vigabatrin, tiagabine, EVT 201 (Evotec Pharmaceuticals), estazolam or any combinations thereof, in free or pharmaceutically acceptable salt form.

In another preferred embodiment, Method I-A, II-A or III-A or any of 10.1-10.38 comprises administering to a patient in need thereof, an effective amount of a compound of the Invention in combination with doxepin in free or pharmaceutically acceptable salt form. Dosages of doxepin can vary in any range known to a person of ordinary skill in the art. In one example, a 10 mg dose of doxepin may be combined with any dosage of a compound of the Invention.

In another embodiment, Method I-A, II-A or III-A or any of 10.1-10.38 comprises administering to a patient in need thereof, an effective amount of a compound of the Invention in combination (including as part of a daily dosage regimen) with an atypical stimulant, e.g., a modafinil, adrafinil, or armodafinil. A regimin incorporating a compound of the Invention with such drugs promotes more regular sleep, and avoids side effects such as psychosis or mania associated with higher levels of such drugs, e.g., in the treatment of bipolar depression, cognition associated with schizophrenia, and excessive sleepiness and fatigue in conditions such as Parkinson's disease and cancer.

In the twelfth aspect, the invention provides use of a compound as described in the following formulae:
12.1 a compound of Formula I, I(a), I(b) or any of formulae 1.1-1.38 as hereinbefore described;
12.2 a compound of Formula II, II(a), II(b) or any of formulae 2.1-2.31, in free or pharmaceutically acceptable salt form as hereinbefore described;
12.3 a compound of Formula III or any of formulae 3.1-3.19 as hereinbefore described;
12.4 a compound of Formula IV or any of formulae 4.1-4.4 as hereinbefore described, in free or pharmaceutically acceptable salt form;
12.5 a Pharmaceutical Composition as described in formula 5.1;
12.6 a Pharmaceutical Composition as described in formula 5.2;
12.7 a Pharmaceutical Composition as described in formula 5.3;
12.8 a Pharmaceutical Composition as described in formula 5.4;
12.9 a Pharmaceutical Composition as described in formula 5.5;
12.10 a Depot Composition of any of formulae 6.1-6.5; or
12.11 Composition of any of formulae P.1-P.7 as hereinbefore described;
(in the manufacture of a medicament) for the treatment or prophylaxis of one or more disorders as disclosed hereinbefore, e.g., in any of Method I or III, any of 8.1-8.52, Method II, any of 9.1-9.16, Methods I-A, II-A or III-A, any of 10.1-10.38.

In the thirteenth aspect, the invention provides a pharmaceutical composition as hereinbefore described for use in the treatment or prophylaxis of one or more disorders as disclosed hereinbefore, e.g., in any of Method I or III, any of 8.1-8.52, Method II, any of 9.1-9.16, Methods I-A, II-A or III-A, any of 10.1-10.38, or any methods described in the eleventh or twelfth aspect of the invention.

DETAILED DESCRIPTION OF THE INVENTION

If not otherwise specified or clear from context, the following terms as used herein have the following meetings:
a. "Alkyl" as used herein is a saturated or unsaturated hydrocarbon moiety, e.g., one to twenty-four carbon atoms in length, which may be linear or branched (e.g., n-butyl or tert-butyl), preferably linear, saturated or unsaturated unless otherwise specified. For example, "$C_{1-24}$ alkyl" denotes alkyl having 1 to 24 carbon atoms. In one embodiment, alkyl is optionally substituted with one or more hydroxy or $C_{1-22}$alkoxy (e.g., ethoxy) groups. In another embodiment, alkyl contains 1 to 24 carbon atoms, preferably straight chain and optionally saturated or unsaturated, for example $R_1$ is an alkyl chain containing 1 to 24 carbon atoms, e.g., 6-15 carbon atoms, 16-24 carbon atoms, e.g., so that together with the —C(O)— to which it attaches, e.g., when cleaved from the compound, forms the residue of a natural or unnatural, saturated or unsaturated fatty acid. In still another embodiment, alkyl contains 1 to 6 carbon atoms.

Unless otherwise indicated, the compounds of the Invention includes the compounds of Formula I, I(a), I(b) or any of formulae 1.1-1.38 as hereinbefore described, Formula II, II(a), II(b) or any of formulae 2.1-2.31, in free or pharmaceutically acceptable salt form; or a compound of Formula III or any of formulae 3.1-3.19 as hereinbefore described; and a compound of Formula IV or any of formulae 4.1-4.4 as hereinbefore described, in free or pharmaceutically acceptable salt form. In certain embodiment, e.g., depot formulation, the compound of Formula Q is also included in the compounds of the invention.

The compounds of Formula II, II(a), II(b) or any of formulae 2.1-2.31 and the compounds of Formula IV or any of formulae 4.1-4.4 as hereinbefore described, may exist in free or salt, e.g., as acid addition salt, form. An acid-addition salt of a compound of the invention which is sufficiently basic, for example, an acid-addition salt with, for example, an inorganic or organic acid, for example hydrochloric, hydrobromic, sulphuric, phosphoric, acid acetic, trifluoroacetic, citric, maleic acid, toluene sulfonic, propionic, succinic, glycolic, stearic, lactic, malic, tartaric, citric, ascorbic, pamoic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic acid, and the like. In addition a salt of a compound of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)-amine. In a particular embodiment, the salt of the compounds of the Invention is a toluenesulfonic acid addition salt. In another particular embodiment, the salt of the compounds of the Invention is a fumeric acid addition salt. In a particular embodiment, the salt of the compounds of the Invention is a phosphoric acid addition salt.

The compounds of the Invention are intended for use as pharmaceuticals, therefore pharmaceutically acceptable salts are preferred. Salts which are unsuitable for pharmaceutical uses may be useful, for example, for the isolation or purification of free compounds of the Invention, and are therefore also included.

The compounds of the Invention may comprise one or more chiral carbon atoms. The compounds thus exist in individual isomeric, e.g., enantiomeric or diasteriomeric form or as mixtures of individual forms, e.g., racemic/diastereomeric mixtures. Any isomer may be present in which the asymmetric center is in the (R)—, (S)—, or (R, S)— configuration. The invention is to be understood as embracing both individual optically active isomers as well as mixtures (e.g., racemic/diasteromeric mixtures) thereof. Accordingly, the compounds of the Invention may be a racemic mixture or it may be predominantly, e.g., in pure, or substantially pure, isomeric form, e.g., greater than 70% enantiomeric/diastereomeric excess ("ee"), preferably greater than 80% ee, more preferably greater than 90% ee, most preferably greater than 95% ee. The purification of said isomers and the separation of said isomeric mixtures may be accomplished by standard techniques known in the art (e.g., column chromatography, preparative TLC, preparative HPLC, simulated moving bed and the like).

Geometric isomers by nature of substituents about a double bond or a ring may be present in cis (Z) or trans (E) form, and both isomeric forms are encompassed within the scope of this invention.

The Compounds of the Invention exist in prodrug form. The term "prodrug" is an art recognized term and refers to a drug precursor prior to administration, but generates or releases the active metabolite in vivo following administration, via some chemical or physiological process. For example, the compounds of Formula I et seq. will be cleaved to release the active compound:

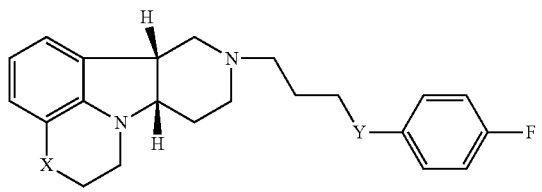

wherein X is —N(H)—, —N($C_{1-6}$alkyl)- or —O—; Y is —C(O)—, —O— or —C(H)($OR^4$)—; and $R^4$ is H. The compounds of Formula II et seq. will be cleaved to release the active compound:

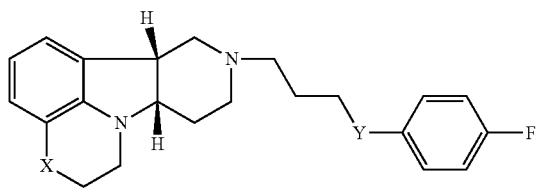

wherein X is —N(H)—; Y is —C(O)—, —O— or —C(H)($OR^4$)—; and $R^4$ is H. The compounds of Formula III et seq. will be cleaved to release the active compound:

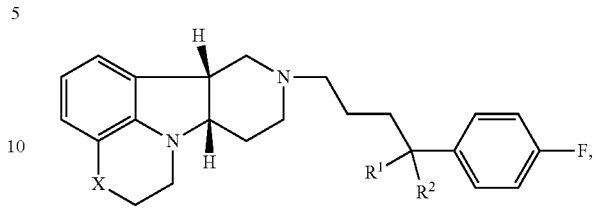

wherein X is —N(H)—, —N($C_{1-4}$alkyl)- or —O—; $R^1$ is H or $C_{1-6}$alkyl (e.g., methyl); and $R^2$ is H or $OR^3$ wherein $R^3$ is H, provided that $R^1$ and $R^2$ are not both H, and $R^1$ and $R^3$ are not both H. The compounds of Formula IV et seq. will be cleaved to release the active compound:

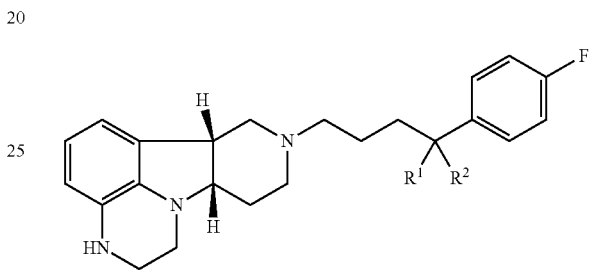

wherein $R^1$ is H or $C_{1-6}$alkyl (e.g., methyl); $R^2$ is H or $OR^3$ wherein $R^3$ is H; provided that $R^1$ and $R^2$ are not both H, and $R^1$ and $R^3$ are not both H.

The prodrug compounds of the Invention are particularly useful for sustained- and/or delayed release so as to achieve a long acting effect, e.g., wherein the active compounds as hereinbefore described or the active compound of Formula Q are released over a period of from about 7 to about 14 to about 30 to about 180 days, preferably over about 30 or about 60 or about 90 days, for example as described in any of formulae 6.1-6.5 or 5.1-5.5 which comprises a viscosity enhancing agent as discussed above. Preferably, the sustained and/or delayed-release formulation is an injectable formulation.

Alternatively and/or additionally, the compounds of the Invention and the Compound of Formula Q may be included as a depot formulation, e.g., by dispersing, dissolving or encapsulating the compounds of the Invention in a polymeric matrix as described in any of composition 6.1-6.5, such that the compound is continually released as the polymer degrades over time. The release of the compounds of the Invention or the Compound of Formula Q from the polymeric matrix provides for the controlled- and/or delayed- and/or sustained-release of the compounds, e.g., from the pharmaceutical depot composition, into a subject, for example a warm-blooded animal such as man, to which the pharmaceutical depot is administered. Thus, the pharmaceutical depot delivers the active compounds described hereinbefore or the Compound of Formula Q to the subject at concentrations effective for treatment of the particular disease or medical condition over a sustained period of time, e.g., 7-180 days, preferably about 7 or about 14 or about 30, about 60 or about 90 days.

Polymers useful for the polymeric matrix in the Composition of the Invention (e.g., Depot composition of any of Formulae 6.1-6.5) may include a polyester of a hydroxyfatty acid and derivatives thereof or other agents such as polylactic acid, polyglycolic acid, polycitric acid, polymalic acid, poly-beta.-hydroxybutyric acid, epsilon.-capro-lactone ring opening polymer, lactic acid-glycolic acid copolymer, 2-hydroxybutyric acid-glycolic acid copolymer, polylactic acid-polyethyleneglycol copolymer or polyglycolic acid-polyethyleneglycol copolymer), a polymer of an alkyl alpha-cyanoacrylate (for example poly(butyl 2-cyanoacrylate)), a polyalkylene oxalate (for example polytrimethylene oxalate or polytetramethylene oxalate), a polyortho ester, a polycarbonate (for example polyethylene carbonate or polyethylenepropylene carbonate), a polyortho-carbonate, a polyamino acid (for example poly-gamma.-L-alanine, poly-.gamma.-benzyl-L-glutamic acid or poly-y-methyl-L-glutamic acid), a hyaluronic acid ester, and the like, and one or more of these polymers can be used.

If the polymers are copolymers, they may be any of random, block and/or graft copolymers. When the above alpha-hydroxycarboxylic acids, hydroxydicarboxylic acids and hydroxytricarboxylic acids have optical activity in their molecules, any one of D-isomers, L-isomers and/or DL-isomers may be used. Among others, alpha-hydroxycarboxylic acid polymer (preferably lactic acid-glycolic acid polymer), its ester, poly-alpha-cyanoacrylic acid esters, etc. may be used, and lactic acid-glycolic acid copolymer (also referred to as poly(lactide-alpha-glycolide) or poly(lactic-co-glycolic acid), and hereinafter referred to as PLGA) are preferred. Thus, in one aspect the polymer useful for the polymeric matrix is PLGA. As used herein, the term PLGA includes polymers of lactic acid (also referred to as polylactide, poly(lactic acid), or PLA). Most preferably, the polymer is the biodegradable poly(d,l-lactide-co-glycolide) polymer.

In a preferred embodiment, the polymeric matrix of the invention is a biocompatible and biodegradable polymeric material. The term "biocompatible" is defined as a polymeric material that is not toxic, is not carcinogenic, and does not significantly induce inflammation in body tissues. The matrix material should be biodegradable wherein the polymeric material should degrade by bodily processes to products readily disposable by the body and should not accumulate in the body. The products of the biodegradation should also be biocompatible with the body in that the polymeric matrix is biocompatible with the body. Particular useful examples of polymeric matrix materials include poly (glycolic acid), poly-D,L-lactic acid, poly-L-lactic acid, copolymers of the foregoing, poly(aliphatic carboxylic acids), copolyoxalates, polycaprolactone, polydioxonone, poly(ortho carbonates), poly(acetals), poly(lactic acid-caprolactone), polyorthoesters, poly(glycolic acid-caprolactone), polyanhydrides, and natural polymers including albumin, casein, and waxes, such as, glycerol mono- and distearate, and the like. The preferred polymer for use in the practice of this invention is dl(polylactide-co-glycolide). It is preferred that the molar ratio of lactide to glycolide in such a copolymer be in the range of from about 75:25 to 50:50.

Useful PLGA polymers may have a weight-average molecular weight of from about 5,000 to 500,000 daltons, preferably about 150,000 daltons. Dependent on the rate of degradation to be achieved, different molecular weight of polymers may be used. For a diffusional mechanism of drug release, the polymer should remain intact until all of the drug is released from the polymeric matrix and then degrade. The drug can also be released from the polymeric matrix as the polymeric excipient bioerodes.

The PLGA may be prepared by any conventional method, or may be commercially available. For example, PLGA can be produced by ring-opening polymerisation with a suitable catalyst from cyclic lactide, glycolide, etc. (see EP-0058481B2; Effects of polymerization variables on PLGA properties: molecular weight, composition and chain structure).

It is believed that PLGA is biodegradable by means of the degradation of the entire solid polymer composition, due to the break-down of hydrolysable and enzymatically cleavable ester linkages under biological conditions (for example in the presence of water and biological enzymes found in tissues of warm-blooded animals such as humans) to form lactic acid and glycolic acid. Both lactic acid and glycolic acid are water-soluble, non-toxic products of normal metabolism, which may further biodegrade to form carbon dioxide and water. In other words, PLGA is believed to degrade by means of hydrolysis of its ester groups in the presence of water, for example in the body of a warm-blooded animal such as man, to produce lactic acid and glycolic acid and create the acidic microclimate. Lactic and glycolic acid are by-products of various metabolic pathways in the body of a warm-blooded animal such as man under normal physiological conditions and therefore are well tolerated and produce minimal systemic toxicity.

In another embodiment, the polymeric matrix useful for the invention may comprise a star polymer wherein the structure of the polyester is star-shaped. These polyesters have a single polyol residue as a central moiety surrounded by acid residue chains. The polyol moiety may be, e. g., glucose or, e. g., mannitol. These esters are known and described in GB 2,145,422 and in U.S. Pat. No. 5,538,739, the contents of which are incorporated by reference.

The star polymers may be prepared using polyhydroxy compounds, e. g., polyol, e. g., glucose or mannitol as the initiator. The polyol contains at least 3 hydroxy groups and has a molecular weight of up to about 20,000 Daltons, with at least 1, preferably at least 2, e. g., as a mean 3 of the hydroxy groups of the polyol being in the form of ester groups, which contain polylactide or co-polylactide chains. The branched polyesters, e. g., poly (d, 1-lactide-co-glycolide) have a central glucose moiety having rays of linear polylactide chains.

The depot composition of the invention (e.g., compositions of any of formulae 6.1-6.5) as hereinbefore described may comprise the polymer in the form of microparticles or nanoparticles, or in a liquid form, with the compounds of the Invention dispersed or encapsulated therein. "Microparticles" is meant solid particles that contain the compounds of the Invention either in solution or in solid form wherein such compound is dispersed or dissolved within the polymer that serves as the matrix of the particle. By an appropriate selection of polymeric materials, a microparticle formulation can be made in which the resulting microparticles exhibit both diffusional release and biodegradation release properties.

When the polymer is in the form of microparticles, the microparticles may be prepared using any appropriate method, such as by a solvent evaporation or solvent extraction method. For example, in the solvent evaporation method, the compounds of the Invention and the polymer may be dissolved in a volatile organic solvent (for example a ketone such as acetone, a halogenated hydrocarbon such as chloroform or methylene chloride, a halogenated aromatic hydrocarbon, a cyclic ether such as dioxane, an ester such as ethyl acetate, a nitrile such as acetonitrile, or an alcohol such as ethanol) and dispersed in an aqueous phase containing a suitable emulsion stabiliser (for example polyvinyl alcohol, PVA). The organic solvent is then evaporated to provide microparticles with the compounds of the Invention encapsulated therein. In the solvent extraction method, the compounds of the Invention and polymer may be dissolved in a polar solvent (such as acetonitrile, dichloromethane, methanol, ethyl acetate or methyl formate) and then dispersed in an aqueous phase (such as a water/PVA solution). An emulsion is produced to provide microparticles with the compounds of the Invention encapsulated therein. Spray drying is an alternative manufacturing technique for preparing the microparticles.

Another method for preparing the microparticles of the invention is also described in both U.S. Pat. Nos. 4,389,330 and 4,530,840.

The microparticle of the present invention can be prepared by any method capable of producing microparticles in a size range acceptable for use in an injectable composition. One preferred method of preparation is that described in U.S. Pat. No. 4,389,330. In this method the active agent is dissolved or dispersed in an appropriate solvent. To the agent-containing medium is added the polymeric matrix material in an amount relative to the active ingredient that provides a product having the desired loading of active agent. Optionally, all of the ingredients of the microparticle product can be blended in the solvent medium together.

Solvents for the compounds of the Invention or the compound of Formula Q and the polymeric matrix material that can be employed in the practice of the present invention include organic solvents, such as acetone; halogenated hydrocarbons, such as chloroform, methylene chloride, and the like; aromatic hydrocarbon compounds; halogenated aromatic hydrocarbon compounds; cyclic ethers; alcohols, such as, benzyl alcohol; ethyl acetate; and the like. In one embodiment, the solvent for use in the practice of the present invention may be a mixture of benzyl alcohol and ethyl acetate. Further information for the preparation of microparticles useful for the invention can be found in U.S. Patent Publication Number 2008/0069885, the contents of which are incorporated herein by reference in their entirety.

The amount of the compounds of the Invention or the compounds of Formula Q incorporated in the microparticles usually ranges from about 1 wt % to about 90 wt. %, preferably 30 to 50 wt. %, more preferably 35 to 40 wt. %. By weight % is meant parts of the compounds of the Invention per total weight of microparticle.

The pharmaceutical depot may comprise a pharmaceutically-acceptable diluent or carrier, such as a water miscible diluent or carrier.

Details of Osmotic-controlled Release Oral delivery System composition may be found in EP 1 539 115 (U.S. Pub. No. 2009/0202631) and WO 2000/35419, the contents of each of which are incorporated by reference in their entirety.

A "therapeutically effective amount" is any amount of the compounds of the invention (for example as contained in the pharmaceutical depot) which, when administered to a subject suffering from a disease or disorder, is effective to cause a reduction, remission, or regression of the disease or disorder over the period of time as intended for the treatment.

Dosages employed in practicing the present invention will of course vary depending, e.g. on the particular disease or condition to be treated, the particular compound of the Invention used, the mode of administration, and the therapy desired. Unless otherwise indicated, an amount of the compound of the Invention for administration (whether administered as a free base or as a salt form) refers to or is based on the amount of the active drug compound in free base form or in pharmaceutically acceptable salt form (i.e., the calculation of the amount is based on the free base amount or pharmaceutically acceptable salt amount and in a non-prodrug form). Therefore, the dosage is based on the amount of the compound of Formula Q, wherein X is —N(CH$_3$)— and Y is —C(=O), in free base form and non-prodrug form (i.e., wherein the prodrug, e.g., substituent R$^5$ of Formula II or the group —C(O)—O—C(R$^a$)(R$^b$)(R$^c$) or —C(R$^6$)(R$^7$)—O—C(O)—R$^8$ on the quarternary ammonium nitrogen of Formula I, is cleaved off wherein X is —N(CH$_3$)— and Y is —C(=O)). In another embodiment, the dosage is based on the amount of the compound of Formula Q, wherein X is —N(CH$_3$)— and Y is —C(=O), in pharmaceutically acceptable salt and non-prodrug form (i.e., wherein the prodrug, e.g., substituent R$^5$ of Formula II or the group —C(O)—O—C(R$^a$)(R$^b$)(R$^c$) or —C(R$^6$)(R$^7$)—O—C(O)—R$^8$ on the quarternary ammonium nitrogen of Formula I, is cleaved off wherein X is —N(CH$_3$)— and Y is —C(=O)).

The compounds of the Invention may be administered by any satisfactory route, including orally, parenterally (intravenously, intramuscular or subcutaneous) or transdermally, but are preferably administered orally. In certain embodiment, the compounds of the Invention, e.g., in depot formulation (e.g., formulae 5.1-5.5 or 6.1-6.5), is preferably administered parenterally, e.g., by injection.

In general, satisfactory results for Method I or III or any of formulae 8.1-8.52 or use of the compounds of the Invention or the compounds of Formula Q as hereinbefore described, e.g. for the treatment of a combination of diseases such as a combination of at least depression, psychosis, e.g., (1) psychosis, e.g., schizophrenia, in a patient suffering from depression; (2) depression in a patient suffering from psychosis, e.g., schizophrenia; (3) mood disorders associated with psychosis, e.g., schizophrenia, or Parkinson's disease; and (4) sleep disorders associated with psychosis, e.g., schizophrenia, or Parkinson's disease, as set forth above are indicated to be obtained on oral administration at dosages of the order from about 1 mg to 100 mg once daily, preferably 2.5 mg-50 mg, e.g., 2.5 mg, 5 mg, 10 mg, 20 mg, 30 mg, 40 mg or 50 mg in free base or pharmaceutically acceptable, non-prodrug form, once daily, preferably via oral administration. Preferably, the daily dosage is 20 mg-40 mg in free base or pharmaceutically acceptable, non-prodrug form. For example, the method of treating schizophrenia or dementia (e.g., in Methods I and III) comprises a daily dosage of 20-40 mg in free base or pharmaceutically acceptable, non-prodrug form.

Satisfactory results for Method II or any of 9.1-9.15, or use of the compounds of the Invention or compounds or Formula Q as hereinbefore described, e.g. for the treatment of sleep disorder alone are indicated to be obtained on oral administration at dosages of the order from about 2.5 mg-5 mg, e.g., 2.5 mg, 3 mg, 4 mg or 5 mg, of a compound of the Invention, in free or pharmaceutically acceptable salt form, once daily, preferably via oral administration.

Satisfactory results for Method I-A or any of 10.1-10.38 are indicated to be obtained at less than 100 mg, preferably less than 50 mg, e.g., less than 40 mg, less than 30 mg, less than 20 mg, less than 10 mg, less than 5 mg, less than 2.5 mg in free base or pharmaceutically acceptable, non-prodrug form, once daily. Satisfactory results for Method II-A or any of 10.1-10.38 are indicated to be obtained at less than 5 mg, preferably less than 2.5 mg in free base or pharmaceutically acceptable, non-prodrug form.

For treatment of the disorders disclosed herein wherein the depot composition is used to achieve longer duration of action, the dosages will be higher relative to the shorter action composition, e.g., higher than 1-100 mg, e.g., 25 mg, 50 mg, 100 mg, 500 mg, 1,000 mg, or greater than 1000 mg in free base or pharmaceutically acceptable, non-prodrug form. For example, for the treatment of psychosis, schizophrenia or dementia (Methods I or III), the weekly biweekly and monthly dosages may be about 100 mg-300 mg (e.g., 140 mg-160 mg), about 250 mg-600 mg (e.g., 280-300 mg) and about 500-1,240 mg (e.g., 600 mg-620 mg) of the compound of the invention based on the free base or pharmaceutically acceptable salt and non-prodrug form. Duration of action of the compounds of the Invention may be controlled by manipulation of the polymer composition, i.e., the polymer:drug ratio and microparticle size. Wherein the composition of the invention is a depot composition, administration by injection is preferred.

The pharmaceutically acceptable salts of the compounds of the Invention can be synthesized from the parent compound which contains a basic or acidic moiety by conventional chemical methods. Generally, such salts can be prepared by reacting the free base forms of these compounds with a stoichiometric amount of the appropriate acid in water or in an organic solvent, or in a mixture of the two; generally, nonaqueous media like ether, ethyl acetate, ethanol, isopropanol, or acetonitrile are preferred. Further details for the preparation of these salts, e.g., toluenesulfonic salt in amorphous or crystal form, may be found in PCT/US08/03340 and/or U.S. Provisional Appl. No. 61/036,069.

Pharmaceutical compositions comprising compounds of the Invention may be prepared using conventional diluents or excipients (an example include, but is not limited to sesame oil) and techniques known in the galenic art. Thus oral dosage forms may include tablets, capsules, solutions, suspensions and the like.

Methods of Making the Compounds of the Invention

The compounds of Formulae I, I(a), I(b) and 1.1-1.38 as hereinbefore described may be prepared by reacting the compound of Formula A, wherein X and Y are defined in any of Formulae I, I(a), I(b) or 1.1-1.37:

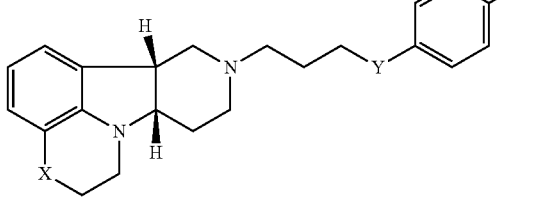

Formula A with L-C($R^6$)($R^7$)—OC(O)—$R^8$ wherein L is a leaving group such as halo, preferably iodo and $R^6$, $R^7$ and $R^8$ are as defined in any of Formulae I, I(a), I(b) or 1.1-1.38, preferably $R^6$ and $R^7$ are H and $R^8$ is $C_9$alkyl. L-C($R^6$)($R^7$)—OC(O)—$R^8$, in turn, may be prepared by reacting Cl—C(O)—$R^8$ with zinc chloride and paraformaldehyde followed by reacting the resulting Cl-L-C($R^6$)($R^7$)—OC(O)—$R^8$ with sodium iodide. $R^6$, $R^7$ and $R^8$ are as defined in any of Formulae I, I(a), I(b) or 1.1-1.38, preferably $R^2$ and $R^3$ are H and $R^1$ is $C_9$alkyl.

The compounds of Formulae II, II(a), II(b) and 2.1-2.31, in free or pharmaceutically acceptable salt form as hereinbefore described may be prepared by reacting the compound of Formula B:

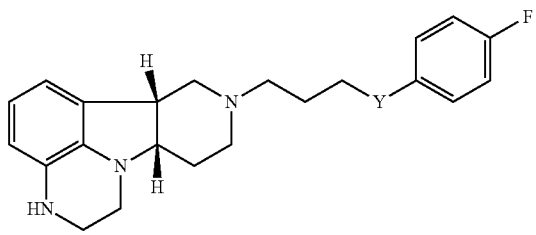

Formula B wherein Y is as defined in any of Formulae II, II(a), II(b) or 2.1-2.31, with triphosgene and a base (e.g., pyridine) in a solvent such as dichloromethane. The resulting chloride-carbonyl derivative of Formula B may then be reacted with HO—C($R^a$)($R^b$)($R^c$) to produce the compounds of any of Formulae II, II(a), II(b) or 2.1-2.31, wherein $R^5$ is —C(O)—O—C($R^a$)($R^b$)($R^c$).

The compounds of Formulae II, II(a), II(b) and 2.1-2.31, wherein $R^5$ is —C($R^6$)($R^7$)—O—C(O)—$R^8$, in free or pharmaceutically acceptable salt form may be prepared by reacting the compound of Formula B with L-C($R^6$)($R^7$)—OC(O)—$R^8$ wherein L is a leaving group such as halo (e.g., iodo) and $R^6$, $R^7$ and $R^8$ are as defined in any of Formulae II, II(a), II(b) and 2.1-2.31.

The compounds of Formula A and Formula B may be prepared by methods disclosed in any of U.S. Pat. No. 8,309,722, WO 2011/133224, WO 2008/112280; U.S. Pat. Nos. 6,548,493; 7,238,690; 6,552,017; 6,713,471; 7,183,282; U.S. RE39680, and U.S. RE39679, the contents of each of which are incorporated by reference in their entirety.

The compounds of Formula III and 3.1-3.19 wherein $R^2$ is —O$R^3$ and $R^3$ is H as hereinbefore described may be may be prepared by reacting Formula C with a Grignard reagent, $R^1$—Mg$X^2$ wherein $X^2$ is halide, e.g., bromide or chloride, preferably bromide, $R^1$ and X are defined in Formula III, e.g., $R^1$ is methyl and X is for example N(CH$_3$), e.g., in a solvent such as tetrahydrofuran or diethyl ether, preferably tetrahydrofuran. The reaction may be summarized in the reaction scheme below:

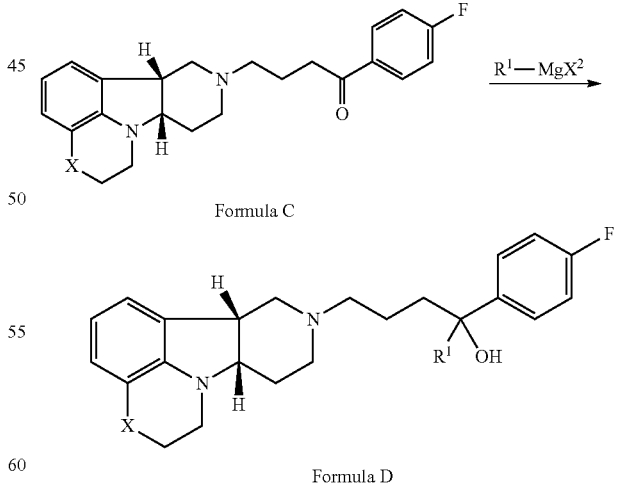

The Compound of Formula III, wherein $R^2$ is —O$R^3$ wherein $R^3$ is $C_{1-6}$alkyl may be prepared by reacting Formula D with $R^3$—OH and BF$_3$.OEt wherein $R^3$ is $C_{1-6}$alkyl. The reaction may be summarized in the reaction scheme below:

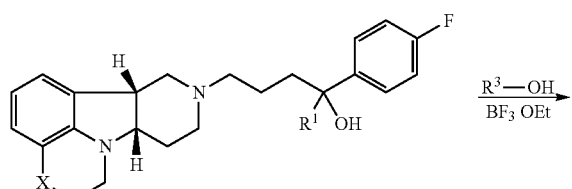

Formula D

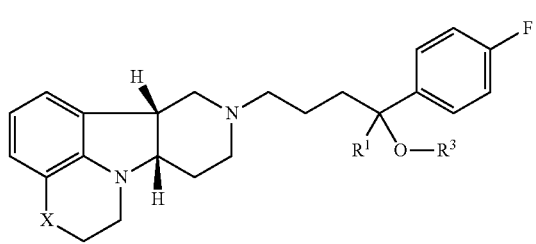

Formula E

The compounds of formulae III and IV may be prepared by using the compounds of Formula D and Formula E wherein X, $R^1$ and $R^3$ are as defined in any of Formulae III, and IV and the procedures described for Formula I, I(a), I(b) and II, II(a) and II(b).

Isolation or purification of the disastereomers of the compounds of the Invention may be achieved by conventional methods known in the art, e.g., column purification, preparative thin layer chromatography, preparative HPLC, crystallization, trituration, simulated moving beds and the like.

Salts of the compounds of the Invention such as Compounds of Formula II and IV may be prepared as similarly described in U.S. Pat. Nos. 6,548,493; 7,238,690; 6,552,017; 6,713,471; 7,183,282; U.S. RE39680; U.S. RE39679; and WO 2009/114181, the contents of each of which are incorporated by reference in their entirety.

General Analytical UPLC Methods for the Determination of Compound Purity

Waters ACQUITY UPLC system: ACQUITY HSS T3 column, 50 mm×2.1 mm, 1.8 μm, 25° C.; mobile phase A, 0.1% formic acid in water/acetonitrile (95/5); mobile phase B, 0.1% formic acid in acetonitrile; gradient, 0.0-3.0 min, 5-95% B; 3.0-4.0 min, 95% B; 4.0-5.0 min, 95-5% B; flow rate 0.3 ml/min; detection at 210-400 nm.

General Preparative HPLC Methods for Compound Purification

All products are purified with a Waters semi-preparative HPLC system, which is equipped with a Delta 600EF pump and a 996 PDA detector. Column: Gemini, AXIA packed, 10 μm C18 110 Å, 250×21.2 mm; mobile phase A, 0.1% formic acid in water; mobile phase B, acetonitrile; gradient is adjusted and optimized based on compound polarity; HPLC run time was 22 min; flow rate was 23.8 ml/min; detection was at 210-350 nm.

Example 1

Synthesis of (6bR,10aS)-8-Decanoyloxymethyl-8-[4-(4-fluoro-phenyl)-4-oxo-butyl]-3-methyl-2,3,6b,7,8,9,10,10a-octahydro-1H-pyrido[3',4':4,5]pyrrolo[1,2,3-de]quinoxalin-8-ium formate

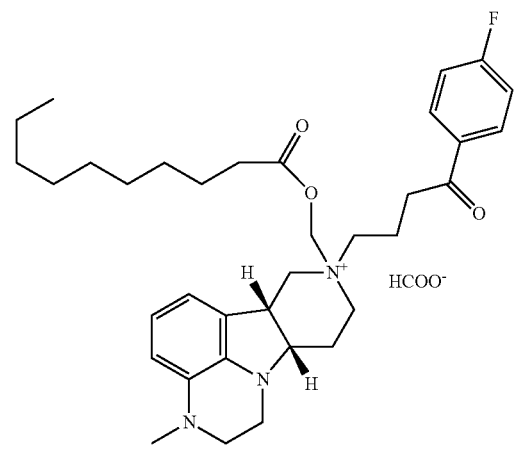

To a solution of decanoyl chloride (1.63 mL 4.2 mmol) and paraformaldehyde (126 mg) in acetone (6 mL) is added zinc chloride. The reaction mixture is stirred at 65° C. overnight. Sodium iodide (1.9 g, 12.6 mmol) is added into the reaction mixture, and the mixture is stirred at room temperature overnight. The reaction mixture is filtered and acetone is removed under reduced pressure. The residue is treated with hexanes, and then filtered. The filtrate is evaporated to dryness under vacuum to give the crude iodomethyl decanoate, which is used in the next step without further purification.

To a solution of the 4-((6bR,10aS)-3-methyl-2,3,6b,9,10,10a-hexahydro-1H,7H-pyrido[3',4':4,5]pyrrolo[1,2,3-de]quinoxalin-8-yl)-1-(4-fluorophenyl)-butan-1-one (27 mg, 0.065 mmol) in methylene chloride (250 uL) is added the crude iodomethyl decanoate (32 mg, 0.10 mmol). The reaction mixture is stirred at room temperature for 3 days, and then purified with a semi-preparative HPLC (Gemini column, AXIA packed, 10 mm C18 110 Å, 250' 21.2 mm; mobile phase A, 0.1% formic acid in water; mobile phase B, 0.1% formic acid in acetonitrile; gradient is adjusted and optimized based on compound polarity; run time 22 min; flow rate 24 mL/min; detection at 210-350 nm) to give (6bR,10aS)-8-Decanoyloxymethyl-8-[4-(4-fluoro-phenyl)-4-oxo-butyl]-3-methyl-2,3,6b,7,8,9,10,10a-octahydro-1H-pyrido[3',4':4,5]pyrrolo[1,2,3-de]quinoxalin-8-ium formate. ESI-MS (m/z, positive mode): 578.4.

Alternatively, the compound of Example 1 may be prepared as follows: To a solution of the 4-((6bR,10aS)-3-methyl-2,3,6b,9,10,10a-hexahydro-1H,7H-pyrido[3',4':4,5]pyrrolo[1,2,3-de]quinoxalin-8-yl)-1-(4-fluorophenyl)-butan-1-one (50.8 mg, 0.13 mmol) in acetonitrile (2.5 mL) is added chloromethyl decanoate (32.7 mg, 0.14 mmol), followed by adding NaI (61 mg, 0.41 mmol). The reaction mixture is stirred at room temperature over a weekend, and then filtered. The obtained filtrate is purified with a semi-preparative HPLC using a gradient of 0-48% B (gradient curve 4) to give (6bR,10aS)-8-decanoyloxymethyl-8-[4-(4-fluoro-phenyl)-4-oxo-buty]-3-methyl-2,3,6b,7,8,9,10,10a-octahydro-1H-pyrido[3',4':4,5]pyrrolo[1,2,3-de]quinoxalin- 8-ium formate (20 mg, 25% yield). UPLC retention time: 3.29 min. ESI-MS (ink, positive mode): 578.3.

Example 1B

Synthesis of (6bR,10aS)-8-[4-(4-fluoro-phenyl)-4-oxo-butyl]-8-isopropoxycarbonyloxymethyl-3-methyl-2,3,6b,7,8,9,10,10a-octahydro-1H-pyrido[3',4':4,5]pyrrolo[1,2,3-de]quinoxalin-8-ium formate

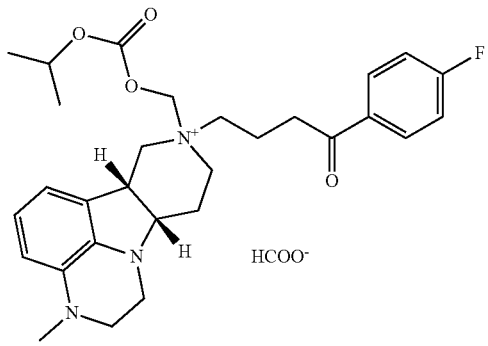

To a solution of the 4-((6bR,10aS)-3-methyl-2,3,6b,9,10,10a-hexahydro-1H,7H-pyrido[3',4':4,5]pyrrolo[1,2,3-de]quinoxalin-8-yl)-1-(4-fluorophenyl)-butan-1-one (48.0 mg, 0.12 mmol) in acetonitrile (2.0 mL) is added chloromethyl isopropyl carbonate (25.0 mg, 0.16 mmol), followed by adding NaI (60.0 mg, 0.40 mmol). The reaction mixture is stirred at room temperature over a weekend, and then filtered. The obtained filtrate is purified with a semi-preparative HPLC using a gradient of 0-35% B (gradient curve 4) to give (6bR,10aS)-8-[4-(4-fluoro-phenyl)-4-oxo-butyl]-8-isopropoxycarbonyloxymethyl-3-methyl-2,3,6b,7,8,9,10,10a-octahydro-1H-pyrido[3',4':4,5]pyrrolo[1,2,3-de]quinoxalin-8-ium formate (50 mg, 75% yield). UPLC retention time: 2.49 min. ESI-MS (m/z, positive mode): 510.3.

Example 1C

Synthesis of (6bR,10aS)-8-(2,2-dimethyl-propionyloxymethyl)-8-[4-(4-fluoro-phenyl)-4-oxo-butyl]-3-methyl-2,3,6b,7,8,9,10,10a-octahydro-1H-pyrido[3',4':4,5]pyrrolo[1,2,3-de]quinoxalin-8-ium formate

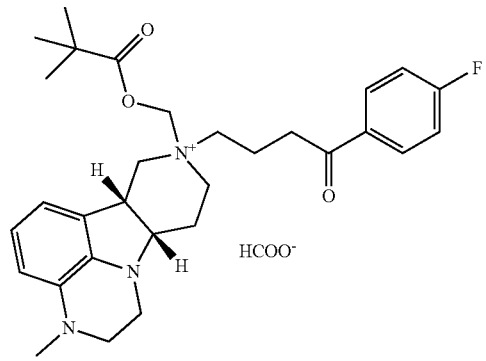

To a solution of the 4-((6bR,10aS)-3-methyl-2,3,6b,9,10,10a-hexahydro-1H,7H-pyrido[3',4':4,5]pyrrolo[1,2,3-de]quinoxalin-8-yl)-1-(4-fluorophenyl)-butan-1-one (49.0 mg, 0.12 mmol) in acetonitrile (3.0 mL) is added chloromethyl pivalate (19 µL, 0.12 mmol), followed by adding NaI (50.0 mg, 0.33 mmol). The reaction mixture is stirred at room temperature overnight, and then filtered. The obtained filtrate is purified with a semi-preparative HPLC using a gradient of 0-35% B (gradient curve 4) to give (6bR,10aS)-8-(2,2-dimethyl-propionyloxymethyl)-8-[4-(4-fluoro-phenyl)-4-oxo-butyl]-3-methyl-2,3,6b,7,8,9,10,10a-octahydro-1H-pyrido[3',4':4,5]pyrrolo[1,2,3-de]quinoxalin-8-ium formate. UPLC retention time: 2.48 min ESI-MS (m/z, positive mode): 508.3.

Example 1D

Synthesis of (6bR,10aS)-8-[4-(4-fluoro-phenyl)-4-oxo-butyl]-8-hexylcarbamoyloxymethyl-3-methyl-2,3,6b,7,8,9,10,10a-octahydro-1H-pyrido[3',4':4,5]pyrrolo[1,2,3-de]quinoxalin-8-ium formate

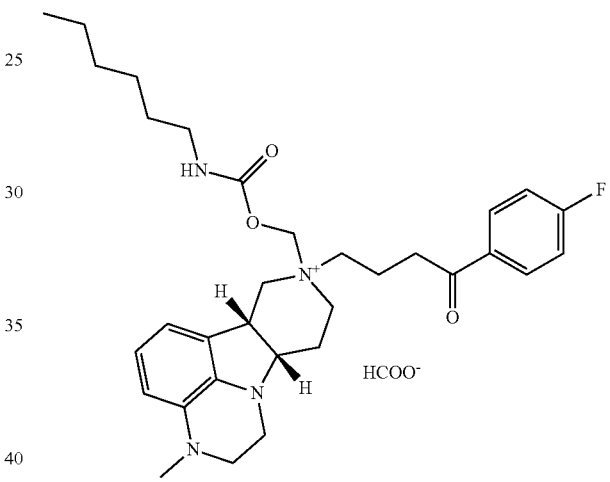

A solution of chloromethyl carbonochloridate (1.0 mL) in CH$_2$Cl$_2$ (10 mL) is cooled to −10° C., and then a solution of hexan-1-amine (1.3 mL) and pyridine (0.9 mL) in CH$_2$Cl$_2$ (2.5 mL) is added dropwise. The reaction mixture is gradually warmed up to room temperature and then stirred at room temperature for 4 h. The mixture is washed with HCl (1N, 5.0 mL), H$_2$O (20 mL) and Saturated NaHCO$_3$ (5.0 mL), successively, and then dried over MgSO$_4$. After the solvents are removed, the obtained crude chloromethyl hexylcarbamate is used directly in the next step without further purification.

To a solution of the 4-((6bR,10aS)-3-methyl-2,3,6b,9,10,10a-hexahydro-1H,7H-pyrido[3',4':4,5]pyrrolo[1,2,3-de]quinoxalin-8-yl)-1-(4-fluorophenyl)-butan-1-one (54 mg, 0.14 mmol) in acetonitrile (1.0 mL) is added crude chloromethyl hexylcarbamate (86 mg, 0.41 mmol), followed by adding NaI (65 mg, 0.41 mmol). The reaction mixture is stirred at room temperature overnight, and then filtered. The obtained filtrate is purified with a semi-preparative HPLC using a gradient of 0-30% B (gradient curve 4) to give (6bR,10aS)-8-[4-(4-fluoro-phenyl)-4-oxo-butyl]-8-hexylcarbamoyloxymethyl-3-methyl-2,3,6b,7,8,9,10,10a-octahydro-1H-pyrido[3',4':4,5]pyrrolo[1,2,3-de]quinoxalin-8-ium formate. UPLC retention time: 2.04 min. ESI-MS (m/z, positive mode): 551.3.

Example 2

Pharmacokinetic Evaluation of the Prodrugs in Rats

Pharmacokinetic Evaluation of the Prodrugs may be carried as described or similarly described below or in WO 2011/084846, the contents of which are incorporated by reference in their entirety.

Animals: Male Sprague-Dawley rats (approximately 24 rats) may be used in each study. Rats may be housed 2 per cage with ad libitum chow and water. Environmental conditions in the housing room may be 64-67° F., 30% to 70% relative humidity, and 12:12-h light:dark cycle.

Test Compounds: An amount of each test compound may be suspended in the vehicle to yield a suspension comprising the equivalent of 3 mg of the compound in free base and non-prodrug form, in 0.3 mL.

Pharmacokinetics study: Rats may be dosed IM by means of a 23 gauge, 1 in. needle with 1 cc syringe. 0.3 mL suspension may be withdrawn from the vial containing the test compound. The rat may be injected in the muscles of the hind limb after anesthesia with isotlourane. Blood samples may be collected via a lateral tail vein after brief anesthesia with isoflourane. A 27½G needle and 1 cc syringe without an anticoagulant may be used for the blood collection. Approximately 250 μL of whole blood may be collected at each sampling time point of 6 hours, 24 hours and 2, 5, 7, 9, 12, 14 days after administration. Approximately 450 μL of whole blood may be collected at sampling time points of 21, 28 and 35 days. Once collected, whole blood may immediately be transferred to tubes containing $K_2$ EDTA, inverted 10-15 times and immediately placed on ice. The tubes may be centrifuged for 2 minutes at >14,000×g (11500 RPM using Eppendorf Centrifuge 5417C, F45-30-11 rotor) at 4-8° C. to separate plasma. Plasma samples may be transferred to labeled plain tubes (MICROTAINER®; MFG # BD5962) and stored frozen at <-70° C.

Data Analysis: Drug concentrations in plasma samples may be analyzed by liquid chromatography-mass spectroscopy using appropriate parameters for each compound. Half-life, volume of distribution, clearance, maximal concentration, and AUC may be calculated by using WinNonlin software, version 5.2 (Pharsight, St. Louis, Mo.).

The Results will show that the prodrug compounds of the invention have a longer $T_{max}$ and/or $T_{1/2}$ than the parent compound (e.g., compound of Formula Q, e.g., wherein X is —C(CH$_3$)— and Y is —C(O)— or the active compound hereinbefore described).

The invention claimed is:

1. A pharmaceutical composition comprising:
(i) a compound of Formula Q:

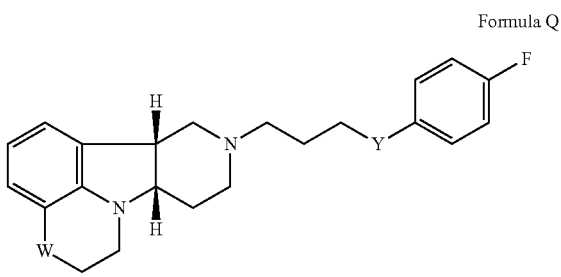

Formula Q wherein:
W is —N(H)— or —N(CH$_3$)—; and
Y is —C(=O)— or —O—;
in free base or pharmaceutically acceptable salt form;
(ii) a polymeric matrix; and
(iii) a vehicle comprising a viscosity enhancing agent.

2. The pharmaceutical composition according to claim 1, wherein the compound of Formula Q is either dissolved in the polymeric matrix or dispersed in the polymeric matrix.

3. The pharmaceutical composition according to claim 1, wherein the polymeric matrix comprises one or more polymers selected from the group consisting of poly(lactic acid), poly(glycolic acid), poly(citric acid), poly(malic acid), poly(beta-hydroxybutyric acid), lactic acid-glycolic acid copolymer, poly(lactide-co-glycolide), 2-hydroxybutyric acid-glycolic acid copolymer, poly(lactic acid)-poly(ethylene glycol) copolymer, poly(glycolic acid)-poly(ethylene glycol) copolymer, a poly(alkyl alpha-cyanoacrylate), a poly(alkylene oxalate), a poly(orthoester), a polycarbonate, a poly(orthocarbonate), a polyamino acid, a hyaluronic acid ester, a poly(aliphatic carboxylic acid), a copolyoxalate, a polycaprolactone, a polydioxanone, a poly(acetal), a poly(lactic acid-caprolactone), and a poly(glycolic acid-caprolactone).

4. The pharmaceutical composition according to claim 3, wherein the polymeric matrix comprises a poly(D,L-lactide-co-glycolide) polymer.

5. The pharmaceutical composition according to claim 4, wherein the polymeric matrix is a microspheric polymeric matrix comprising a biodegradable poly(D,L-lactide-co-glycolide) polymer.

6. The pharmaceutical composition according to claim 1, wherein the pharmaceutical composition is formulated as a sustained-release and/or delayed release injectable composition.

7. The pharmaceutical composition according to claim 1, wherein the viscosity enhancing agent is a sodium carboxymethylcellulose.

8. The pharmaceutical composition according to claim 1, wherein the vehicle further comprises a pharmaceutically acceptable diluent or carrier.

9. The pharmaceutical composition according to claim 1, wherein:
W is —N(CH$_3$)—; and
Y is —C(=O)—.

10. The pharmaceutical composition according to claim 9, wherein the compound of Formula Q is in pharmaceutically acceptable salt form.

11. The pharmaceutical composition according to claim 10, wherein the pharmaceutically acceptable salt form is a toluenesulfonic acid addition salt form.

12. The pharmaceutical composition according to claim 11, wherein the compound of Formula Q is either dissolved in the polymeric matrix or dispersed in the polymeric matrix.

13. The pharmaceutical composition according to claim 12, wherein the polymeric matrix comprises one or more polymers selected from the group consisting of poly(lactic acid), poly(glycolic acid), poly(citric acid), poly(malic acid), poly(beta-hydroxybutyric acid), lactic acid-glycolic acid copolymer, poly(lactide-co-glycolide), 2-hydroxybutyric acid-glycolic acid copolymer, poly(lactic acid)-poly(ethylene glycol) copolymer, poly(glycolic acid)-poly(ethylene glycol) copolymer, a poly(alkyl alpha-cyanoacrylate), a poly(alkylene oxalate), a poly(orthoester), a polycarbonate, a poly(orthocarbonate), a polyamino acid, a hyaluronic acid ester, a poly(aliphatic carboxylic acid), a copolyoxalate, a polycaprolactone, a polydioxanone, a poly(acetal), a poly(lactic acid-caprolactone), and a poly(glycolic acid-caprolactone).

14. The pharmaceutical composition according to claim 13, wherein the polymeric matrix comprises a poly(D,L-lactide-co-glycolide) polymer.

15. The pharmaceutical composition according to claim 14, wherein the polymeric matrix is a microspheric polymeric matrix comprising a biodegradable poly(D,L-lactide-co-glycolide) polymer.

16. The pharmaceutical composition according to claim 15, wherein the pharmaceutical composition is formulated as a sustained-release and/or delayed release injectable composition.

17. The pharmaceutical composition according to claim 16, wherein the viscosity enhancing agent is a sodium carboxymethylcellulose.

* * * * *